(12) United States Patent
Mohanty et al.

(10) Patent No.: US 12,257,448 B2
(45) Date of Patent: Mar. 25, 2025

(54) IMAGE GUIDED VARIABLE SPOT STIMULATION-BASED ELECTROPHYSIOLOGY ASSESSMENT DEVICE TO DETERMINE CHANGES IN THE FUNCTIONAL HEALTH OF BIOLOGICAL SAMPLES DURING DISEASE PROGRESSION AND THERAPY

(71) Applicant: Nanoscope Instruments, Inc., Bedford, TX (US)

(72) Inventors: Samarendra Kumar Mohanty, Southlake, TX (US); Sanghoon Kim, Bedford, TX (US); Michael Carlson, Rowlett, TX (US); Subrata Batabyal, Arlington, TX (US)

(73) Assignee: NANOSCOPE INSTRUMENTS, INC., Bedford, TX (US)

( * ) Notice: Subject to any disclaimer, the term of this patent is extended or adjusted under 35 U.S.C. 154(b) by 0 days.

(21) Appl. No.: 18/511,752

(22) Filed: Nov. 16, 2023

(65) Prior Publication Data

US 2024/0157169 A1    May 16, 2024

Related U.S. Application Data

(60) Provisional application No. 63/383,979, filed on Nov. 16, 2022.

(51) Int. Cl.
*A61N 5/06* (2006.01)
*A61B 3/10* (2006.01)
(Continued)

(52) U.S. Cl.
CPC ............ *A61N 5/0613* (2013.01); *A61B 3/102* (2013.01); *A61B 5/398* (2021.01); *A61B 5/4842* (2013.01);
(Continued)

(58) Field of Classification Search
CPC ...... A61N 5/06–2005/073; A61B 18/20–18/28
(Continued)

(56) References Cited

U.S. PATENT DOCUMENTS

2006/0184214 A1 * 8/2006 McDaniel ............ A61N 5/0616
607/89
2014/0285812 A1 * 9/2014 Levitz .................. A61B 5/0066
356/479
(Continued)

FOREIGN PATENT DOCUMENTS

CA       3153866 A1 *  4/2021  ............... A61B 3/12
CN   115399729 A  * 11/2022
(Continued)

OTHER PUBLICATIONS

Tomczewski et al. "Light-adapted flicker optoretinograms captured with a spatio-temporal optical coherence-tomography (STOC-T) system." Biomedical Optics Express, (Mar. 17, 2022), pp. 2186-2201 vol. 13 (4). Retrieved from the Internet Feb. 28, 2024. https://opg.optica.org/boe/fulltext.cfm?uri=boe-13-4-2186&id=470565.
(Continued)

*Primary Examiner* — Jonathan T Kuo
*Assistant Examiner* — Vynn V Huh
(74) *Attorney, Agent, or Firm* — Shirley A. Recipon

(57) ABSTRACT

The present invention generally relates to an image guided variable spot stimulation-based electrophysiology assessment device for different biomedical applications. Specifically, the invention relates to application of the device to perform image-guided functional assessment upon variable spot optical stimulation of light-activatable biological specimens to determine changes in the functional health during disease progression and therapy. More specifically, the
(Continued)

invention relates to the application of the device in the diagnosis of visual and neurological disorders.

11 Claims, 13 Drawing Sheets

(51) Int. Cl.
   *A61B 5/00* (2006.01)
   *A61B 5/398* (2021.01)
(52) U.S. Cl.
   CPC .............. *A61N 2005/0626* (2013.01); *A61N 2005/0659* (2013.01)
(58) Field of Classification Search
   USPC ....................................................... 606/2–19
   See application file for complete search history.

(56) References Cited

U.S. PATENT DOCUMENTS

| | | | |
|---|---|---|---|
| 2015/0371383 A1* | 12/2015 | Chabrier | G06T 7/0014 600/476 |
| 2019/0282088 A1 | 9/2019 | Mohanty et al. | |
| 2020/0022575 A1 | 1/2020 | Miller et al. | |
| 2020/0288968 A1* | 9/2020 | Jackson | A61B 3/024 |

FOREIGN PATENT DOCUMENTS

| | | |
|---|---|---|
| WO | 2009089509 A1 | 7/2009 |
| WO | PCTUS2380071 | 11/2023 |

OTHER PUBLICATIONS

Zhu et al. "Near Infrared (NIR) Light Therapy of Eye Diseases: A Review." Int. J. Med. Sci. (Jan. 1, 2021), pp. 109-119. vol. 18(1). [retrieved on Feb. 28, 2024]. Retrieved from the Internet: https://www.ncbi.nlm.nih.gov/pmc/articles/PMC7738953/pdf/ijmsvl 8p0109.
Shan et al. "Effect of Near-Infrared Pulsed Light on the Human Brain Using Electroencephalography." Evidence-Based Complementary and Alternative Medicine, (Mar. 5, 2021), pp. 1-11, vol. 2021, Article ID: 6693916 [retrieved on Feb. 28, 2024]. Retrieved from the Internet: https://www.ncbi.nlm.nih.gov/pmc/articles/PMC7954620/pdf/ECAM2021-6693916.
International Search Report, corresponding PCT/US2023/080071, ISA/US Mar. 6, 2024.
Written Opinion of the International Searching Authority, corresponding PCT/US2023/080071, ISA/US Mar. 6, 2024.

\* cited by examiner

2mm, Std. Cones (3cds/m², Light adapted)

2mm, Std. Rod and Cones (3cd·s/m², Dark adapted)

2 mm, Scotopic Rods (0.01 cds/m², Dark adapted)

4 mm, Scotopic Rods (0.01 cds/m², Dark adapted)

IMAGE GUIDED VARIABLE SPOT STIMULATION-BASED ELECTROPHYSIOLOGY ASSESSMENT DEVICE TO DETERMINE CHANGES IN THE FUNCTIONAL HEALTH OF BIOLOGICAL SAMPLES DURING DISEASE PROGRESSION AND THERAPY

CROSS-REFERENCE

This application claims the benefit of priority to U.S. Provisional application No. 63/383,979, filed Nov. 16, 2022, entitled "IMAGE GUIDED VARIABLE SPOT STIMULATION-BASED ELECTROPHYSIOLOGY ASSESSMENT DEVICE TO DETERMINE CHANGES IN THE FUNCTIONAL HEALTH OF BIOLOGICAL SAMPLES DURING DISEASE PROGRESSION AND THERAPY", and which is hereby incorporated by reference in its entirety. Some references, which may include publications, patents, and patent applications, are cited, and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference were individually incorporated by reference.

STATEMENT REGARDING FEDERALLY SPONSORED RESEARCH OR DEVELOPMENT

This invention was made with funding by Nanoscope Instruments, Inc. The Government has no rights in the invention.

FIELD OF INVENTION

The present invention generally relates to an image guided variable spot stimulation-based electrophysiology assessment device for different biomedical applications. Specifically, the invention relates to the application of the device to perform image-guided functional assessment upon variable spot optical stimulation of light-activatable biological specimens to determine changes in the functional health during disease progression and therapy. More specifically, the invention relates to the application of the device in the diagnosis of visual and neurological disorders.

BACKGROUND OF INVENTION

Retinal disorders are characterized by the dysfunction/degeneration of various retinal layers and photoreceptors at different rates and locations. Advancement of new therapeutic interventions such as gene therapy and cell replacement therapies are dependent on functional measurements at the diseased and treated area. However, isolated functional characterization of a spatially targeted region of the retina such as geographic atrophies or treated areas is often challenged with lack of spatial targetability, and collateral bleeding responses of nearby cells. Therefore, there is a clear need for development of high-resolution ERG based on multi-color variable spot stimulation to discern cellular changes, thus allowing critical evaluation of disease progression and therapeutic intervention in the retina.

SUMMARY OF THE INVENTION

To meet the challenges, the present invention provides an image-guided variable spot light-stimulated electrophysiological device which facilitates targeted stimulation and can have applications in structural/functional imaging and assessments.

Specifically, the present invention combines 3D imaging and electrophysiology capability, including an OCT-guided variable spot ERG platform with real-time imaging guidance for high resolution biomicroscopic imaging and electrophysiology for the structural and functional assessment of the retina as a new tool in the diagnosis and management of retinal diseases.

In an embodiment, the invented device generates photic signals and measures the electrical signals generated by the retina and the visual nervous system. It displays digitized ERG, visual evoked potential (VEP) signals, power spectral and topographic maps. The spatial size of the stimulus field(s) is pre-decided by the user with guidance provided by OCT imaging. Flash/flicker, monochromatic, or white light or onset Contrast Photic stimuli are presented to the desired area(s) of retina of the subject's eye. The evoked signals are analyzed by the software algorithm for temporal filtering and artifact rejection. Data is presented in numerical and graphical form.

In an embodiment, the present invention envisages a device wherein spatiotemporal guidance of light stimulation of the sample consists of OCT and/or fundoscope. In the case of OCT, the three-dimensional imaging is achieved either by use of low coherence broadband light source and spectrograph-camera detector or via swept-source combined with a photodiode-detector.

In yet another embodiment, the present invention comprehends a device comprising an OCT integrated with a stimulating beam of varying wavelengths and operation modes for controlling the spot size of the targeted stimulation wherein the spot size can vary between a diffraction limited spot to a spot covering the whole field of view, for instance.

In yet another embodiment, the present invention contemplates a device comprising image-guided variable-spot stimulation light having different wavelengths, integrated with an electrical signal detection system for functional assessment including electroretinogram (ERG), visually evoked potential (VEP) and other light activatable electrical potential changes.

In yet another embodiment, the present invention provides an OCT-guided variable spot electrophysiology device which can stimulate layer-specific photoreceptors or neural retina or other light-sensitive neurons by a focal plane adjustment at the depth(s) of interest and tuning the wavelength to match the cell type(s) of interest, and/or by photobleaching other cell type(s) with wavelength tuned background light.

In another embodiment, the present invention encompasses an image-guided variable spot device for localized and patterned stimulation with light beams of different wavelengths and spot sizes to monitor activities of specific cell types.

In yet another embodiment, the present invention provides a unique method for multiplexed measurement of different photoreceptors using simultaneous stimulation by multiple light beams of different colors (wavelengths) at different pulse rates (frequencies).

In yet another embodiment, the present invention contemplates spatiotemporal multiplexing for reducing measurement time in case of long-duration measurements at multiple spots.

In yet another embodiment, the present invention comprehends a method for functional mapping of the visual field in a time-efficient manner using pattern stimulation via OCT-vsERG.

In yet another embodiment, the present invention encompasses a method by which the image-guided light stimulation spot can be precisely expanded/contracted with fast and precise scanning control of the deflecting mirrors and the liquid lens, and positioning in the selected area(s) of the retina.

In another embodiment, the present invention provides a method, wherein the image-guided electrophysiological system of different stimulation wavelengths and operation modes generate functional assessments of retina abnormalities including dry AMD, retinitis pigmentosa, cone-rod dystrophy, diabetic macular edema, and diabetic retinopathy.

In yet another embodiment, the present invention comprehends a configuration wherein an indirect fundoscopic imaging is integrated with an OCT guided variable spot electrophysiology system to improve image guidance for targeted stimulation.

In a broader embodiment, the present invention provides a method for evaluation of localized therapeutic effects using image-guided variable spot electrophysiology system with multiple stimulation wavelengths: Gene replacement, optogenetic gene therapy, and regenerative cell (transplant) therapies.

It is contemplated that any embodiment of a method, device or composition described herein can be implemented with respect to any other method, device or composition described herein.

Details associated with the embodiments described above and others are described below.

Other objects' features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF DRAWINGS

The following drawings illustrate by way of example and not limitation. For the sake of brevity and clarity, every feature of a given structure is not always labeled in every figure in which that structure appears. The following drawings form part of the present specification and are included to further demonstrate certain aspects of the present invention. The invention may be better understood by reference to one or more of these drawings in combination with the detailed description of the specification embodiments presented herein.

DETAILED DESCRIPTION OF THE INVENTION

Figure 1A:
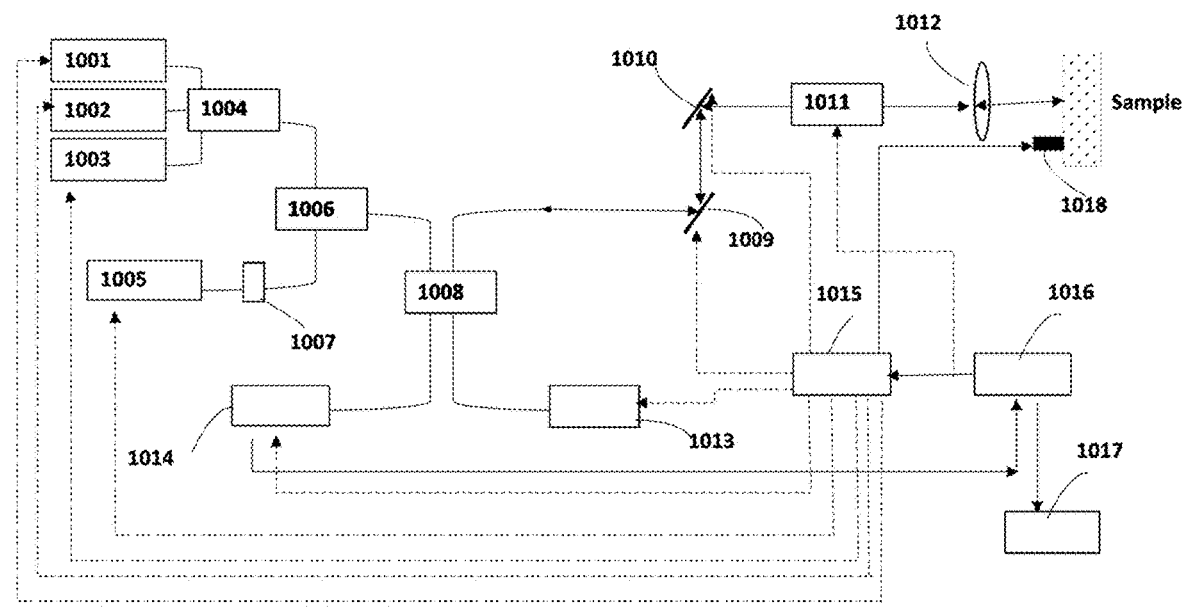
FIG. 1A. Configuration-1 of OCT guided variable spot stimulation and electrophysiology system. 1001: Blue Light Source; 1002: Green Light Source; 1003: Red Light Source; 1004: Beam Combiner-1; 1005: Imaging light source; 1006: Beam Combiner-2; 1007: Laser isolator; 1008: Beam Splitter; 1009: Mirror-1; 1010: Mirror-2; 1011: Dynamic Focusing Element; 1012: Focusing Lens(es); 1013: Reference arm; 1014: Detector; 1015: Microcontroller; 1016: Computer; 1017: Display; 1018: Electrode(s).

Vision loss due to retinal dystrophies including Chorioretinal and outer retinal dystrophies such as dry age-related macular degeneration[1] (dry-AMD) is associated with loss of photoreceptors or Retinal Pigment Epithelium (RPE), involved in visual transduction. Inherited retinal disorders[2,3,4] are becoming the leading cause of blindness in the working age population in developed countries. A significant portion of this population is affected by Retinitis Pigmentosa (RP)[5], followed by Stargardt disease[6,7], and other diseases affecting the photoreceptors. These degenerative diseases are characterized by the degeneration of different types of photoreceptors leading to dysfunction of the retina. Dysfunction or death of photoreceptors leads to loss of signals that initiate visual perception. While RP[8] is associated with loss of rods preceding loss of cones, the reverse is encountered in cone-rod dystrophy where loss of cones leads to loss of rods. With emergence of preventive treatments, early diagnosis of these diseases would help slow down the disease progression. Since there is a wide variation of the spatial-pattern for degeneration in these diseases (e.g., central vision in the case of AMD and peripheral in RP), and the degree of visual loss increases with ageing[9] at different rates, measurement of structural and functional integrity of retina in a spatially-resolved manner can better guide different therapeutic interventions, as and when they become available.

Evoked potentials are used to measure the electrical activity in certain areas of biological specimen. To produce electrical activity of a biological sample of interest, stimulation of specific sensory nerve pathways is required. Although functional response of electrophysiological signal of stimulated biological tissue has been measured, spatially targeted variable spot stimulation of localized area with high resolution has not been realized prior to this invention.

Spatially targeted stimulation is difficult without any imaging guidance and stimulation device co-registered with imaging guidance modality.

The most widely accepted method for functional evaluation of a retina is electroretinography (ERG). ERG measures the electrical responses of various cell types in the retina, including the photoreceptors, inner retinal cells, and the retinal ganglion cells. There are various modes of stimulation for ERG measurements, such as global stimulation, multi-focal stimulation, flickering stimulation, and patterned stimulation to access selective functional information of a retina.

Full-field flash Electroretinogram (ERG) has enabled measurement of overall retinal function[10]. Yet, this technique may not detect retinal defects at early stages of disease. On the other hand, the large spot size stimulation[11, 12] in the existing ERG cannot provide functional information at the resolution necessary to evaluate localized atrophy or therapeutic efficacy. Similarly, the multifocal ERG (mfERG) method[13] that provides a topographical measurement of retinal activity, cannot isolate function at localized regions with signal-to-noise ratio sufficient to discriminate health of different photoreceptors. Therefore, different rod vs. cone ERG protocols have not been implemented for mfERG. Further, conventional mfERG illumination use white light and therefore, cannot distinguish different cone functions.

Further, structural measurements and functional registration at the same locations(s) are necessary for precise diagnosis. To address this challenge, we have developed optical coherence tomography (OCT) and/or fundoscopic image guided ERG based on multi-color variable-spot light stimulation to discern cellular function at high resolution, thus enabling spatially resolved and isolated measurement of retina function with minimal response from unintended region(s), allowing critical evaluation of disease progression and therapeutic interventions.

In an embodiment, the present invention provides a device comprising an OCT guided stimulating light beam integrated with an electrophysiology system with varying wavelengths and operation modes for controlling the spot size of the targeted stimulation, wherein the spot size can vary between diffraction limited spot size to spot covering the whole field of view.

In yet another embodiment, the present invention contemplates a biomicroscopic imaging and electrodiagnostic device that incorporates fundoscope and electrical biosensing hardware for structural and functional assessment of the retina as an aid in the diagnosis and management of retinal disease.

In another embodiment, the present invention encompasses a device wherein spatiotemporal guidance of light stimulation of the sample consists of OCT and/or fundoscope. In the case of OCT, the three-dimensional imaging is generated either by use of low coherence broadband light source and spectrograph-camera detector or via swept-source combined with photodiode-detector.

In yet another embodiment, the present invention comprehends a method by which the image-guided light stimulation spot can be precisely expanded/contracted with fast and precise scanning control of the deflecting mirrors and the liquid lens, and positioning in the selected area(s) of retina. The image-guided variable spot ERG (vsERG) system can measure a signal from as small as diffraction limited spot size to large spot size covering the whole field of view in a controlled (location, size, wavelength, intensity, duration) manner.

In yet another embodiment, the present invention provides OCT guided variable spot ERG system with multiple stimulation wavelengths which allows assessment of different photoreceptors' functions. The OCT guided variable spot ERG system is capable of multi-color stimulation, and the system allows capture of OCT B-scan and enface images for selection of areas of interest and positioning of the stimulation spot(s).

In yet another embodiment, the present invention provides a method for functional mapping of the visual field in a time-efficient manner using pattern stimulation via OCT-vsERG. The real-time structural and functional assessment allows easy decision making for the spatially controlled treatment of the retina.

In yet another embodiment, the present invention encompasses a unique method for multiplexed measurement of different photoreceptors using simultaneous stimulation by multiple light beams of different colors (wavelengths) at different pulse rates (frequencies). For fast electrophysiological responses such as cone response respective to flicker stimulation, multiple stimulations targeting different wavelength dependent light sensitive cells have been realized with frequency multiplexing. Since each type of light sensitive cells have distinct but separated absorption peak, numerous stimulations of different wavelengths can be combined with unique stimulation frequency to extract light response of different types of light activatable cells within the common stimulated area with single measurement. The stimulated cell types only respond to light flicker that matches its absorption peak, and mixed response from individual cells can be deconvolved by averaging acquired electrophysiological signal with respective to corresponding color stimulation time stamps. In addition to temporal averaging, frequency filtering further diminishes contributions from other frequency response by applying notch and band-pass filter.

In yet another embodiment, the present invention contemplates spatiotemporal multiplexing for reducing measurement time in case of long-duration measurements at multiple spots. For electrophysiological that is an order of magnitude longer than stimulation duration and require relaxation time for subsequent stimulation, the invention comprehends a method to stimulate multiple non overlapping areas using a short burst of stimulation to improve signal to noise ratio of averaged signal. In this method, instead of stimulating one location and wait for the full recovery of the stimulated area, the next area is soon stimulated. By stimulating about a significant fraction of total number of spots of interest in each burst stimulation window, the measured electrophysiological signal arising from single set of bursts of stimulation contain linear combination of signal responses from multiple regions. There is an intrinsic time delay between individual stimulation, but since the location and time of the stimulation are known and synchronized, the order of stimulation among various spots of interest are changed. By solving linear equations based on location and time of stimulation, averaged signal from individual spot location can be retrieved.

According to yet another embodiment, the device comprises:
i) an image-guided light stimulation beam allowing for a variable spot size at a sample, for electrophysiological measurements of the sample,
ii) an image-guided light stimulation beam assembly comprising:
an imaging sub-assembly that provides illumination and collection of back-reflected light from the sample for imaging, and comprises near infrared (NIR) light from a low coherence source, and wherein the near infrared (NIR) light is able to be split into a sample beam and a reference beam for interferometric detection to obtain depth resolved images, and
   a light stimulation sub-assembly comprising of light beams of different wavelengths with controllable intensities and/or pulsation rates,
iii) wherein a stimulation beam power at a sample plane ranges from 0.01 to 50 cd·s/m² for each individual stimulation light beam wavelength,
iv) wherein the light stimulation beam is combinable with the sample beam and able to be directed to the sample,
v) wherein the sample is selected from neurons or light-sensitive cells in-vitro or in-vivo,
vi) wherein the region of interest for the electrophysiological measurement on the sample in response to variable spot stimulation is pre-selected and controlled by scanning mirrors for deflecting the stimulation beam(s),
vii) wherein the variable spot size is generated by a dynamic focusing element (such as liquid lens)—for example from diffraction limited spot to the size of field of view,
viii) wherein the light stimulation is able to be targeted in the pre-selected region of interest on the sample,
ix) wherein the light stimulation beam is able to be switched off during preselection of the region of interest for light stimulation, and wherein the preselection of the region of interest is based on morphologic/tomographic imaging,
x) wherein the sample beam for morphologic/tomographic imaging is deliverable via fiber-optic or free-space, and is able to be collimated, and deflected to the sample by the scanning mirrors and optical components,
xi) wherein the optical components are coated with an anti-reflection material for avoiding scattering and multiple reflections,
xii) wherein the back-reflected sample beam for morphologic/tomographic imaging from the sample is able to be routed back to a detector,
xiii) wherein a tomographic image is reconstructable by recording and analysis of interference between the back-reflected sample beam and the reference beam,
xiv) wherein the morphologic/tomographic image is able to be marked with selected regions of variable sizes to match with the light stimulation spots for electrophysiological measurements,
xv) wherein electrophysiological measurement is able to be conducted by electrodes connected to biosensing hardware (for example, Analog to digital converter).

Optionally, it may be that the image guided light stimulation beam, allowing a variable spot size at a sample, for electrophysiological measurement can be a benchtop system or wearable system, and optionally it may be that the wearable system for electrophysiological measurements comprises goggles or eye glasses. Optionally, it may be that the wearable system for electrophysiological measurements consists of goggles or eye glasses.

According to yet another embodiment, there is provided a method wherein spatial-temporal multiplexed variable-spot light stimulated electrophysiological measurements is carried out within a short time enabling improved signal to noise ratio from averaging and reducing measurement time, by:

i) stimulating multiple non-overlapping areas using a short burst of stimulation,
ii) reducing time gap between stimulation at multiple spots,
iii) changing order of synchronized stimulation among various spots of interest,
iv) measuring electrophysiological signal arising from single set of bursts of stimulation at various spots at different locations, and
iv) deconvolving the signal responses from multiple regions to obtain averaged signal from individual spot location.

According to yet another embodiment, there is contemplated a method wherein stimulation frequency multiplexed measurements, utilized to stimulate and recording of multiple light responding cell types with different absorption spectrum at the same stimulation location simultaneously, is conducted by:

i) combining multiple wavelength stimulation beams, modulated at different frequencies,
ii) stimulating different light sensitive cells having distinct but separated absorption peaks,
iii) extracting light response of different types of light activatable cells within the common stimulated area with single measurement,
iv) deconvolving mixed response from individual cells by averaging acquired electrophysiological signal with respective to corresponding color stimulation time stamps, and/or
v) reducing contributions of frequency/wavelength dependent response of the other cell type by notch frequency filtering.

According to yet another embodiment, the present invention provides that localized disease progression or therapeutic effect is measured using image-guided variable spot electrophysiology system with multiple stimulation wavelengths, and identified by:

i) comparing measurements at baseline of healthy/normal and abnormal area(s) with identical stimulation parameters,
ii) comparing spatially localized electrophysiology measurement to earlier time point measurement at the same location(s),
iii) identifying changes of various light sensitive cell type functions with matching stimulation wavelength and/or stimulation intensities,
iv) mapping out electrophysiological function of the visual field by different stimulation patterns such as peripheral stimulation pattern and array stimulation pattern,
v) determining the progression of localized dystrophy or therapeutic improvements by series of enlarging concentric circular stimulations to assess gradient of electrophysiological changes at the localized disease region(s).

In another embodiment, the present invention contemplates a device comprising an OCT guided stimulating light integrated with electrophysiology system consisting of graphical user interface (GUI) software which provides a platform for user interaction, allowing the user to control desired stimulation locations within the field of view of the enface image.

In yet another embodiment, the present invention encompasses a device comprising an OCT guided variable spot electrophysiology system consisting of graphical user interface (GUI) software which allows the initiation of electroretinogram (ERG) when the user selects any specific locations for stimulation on the enface image and prompts the user with a list of stimulation and recording parameters.

In another embodiment, the present invention envisages a device comprising an OCT guided variable spot electrophysiology system consisting of graphical user interface (GUI) software wherein after selection of specific parameters such as stimulation power, duration, time between stimulations and number of stimulations, the software guides the user through the beginning of the image/signal recording process which is automated after the startup phase.

In another embodiment, the present invention comprehends a device for use in method, wherein the said OCT guided stimulating light integrated electrophysiological system of different wavelengths and operation modes can generate functional assessments from a model for, dry AMD, retinitis pigmentosa or cone-rod dystrophy by selectively stimulating rods or cone photoreceptors.

In another embodiment, the present invention contemplates a wearable or a portable benchtop OCT guided variable spot electrophysiology system of different wavelengths and operation modes that can perform (are operable to perform or configured to perform) functional assessments from a model for dry AMD, retinitis pigmentosa or cone-rod dystrophy by selectively stimulating rods or cone photoreceptors.

In another embodiment, the present invention envisages a wearable OCT guided variable spot electrophysiology system wherein the wearable part consists of but not limited to goggles, eye glasses etc.

In another embodiment, the present invention provides Evaluation of localized therapeutic effects using OCT guided variable spot ERG system with multiple stimulation wavelengths: Gene replacement[14], optogenetic gene therapy[15], and regenerative cell[16] (transplant) therapies have promise to restore vision loss in degenerated regions of the retina. Importantly, accurate measurements of visual function would allow for quantitative evaluation of retinal function restoration after therapeutic treatment. This will in turn provide further insight into the efficiency of integration of transduced genes or transplanted cells to enable vision restoration. Use of OCT guided variable spot ERG system enabled measurement of improved visual response in the optogenetic-treated dystrophic retinal region lacking outer retina.

The present disclosure will now be described more fully hereinafter with reference to the accompanying drawings, in which some exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternative are mutually exclusive, although the disclosure supports a definition that refers to only alternatives and "and/or."

The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

Throughout this application, the term "about" is used to indicate that a value includes the standard deviation of error for the device or method being employed to determine the value.

Further, a device or method that is configured in a certain way is configured in at least that way, but it can also be configured in other ways than those specifically described. It may be that the device is operable or configured to perform a function as described herein. This meaning is encompassed within the disclosure of this specification.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an apparatus that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Any embodiment of any of the apparatuses, devices, systems, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

To the extent that any specific disclosure in the aforementioned references or other literature may be considered to anticipate any generic aspect of the present invention, the disclosure of the present invention should be understood to include a proviso or provisos that exclude of disclaim any such species that were previously disclosed. The aspects of the present invention, which are not anticipated by the disclosure of such literature, are also nonobvious from the disclosure of these publications, due at least in part to the unexpectedly superior results disclosed or alleged herein.

Below, the presently disclosed invention will be further described by way of examples, which are provided for illustrative purposes only and accordingly are not to be construed as limiting the scope of the invention.

Examples

We have developed an image guided variable spot stimulation-based electrophysiology assessment device for different biomedical applications. With image-guidance, the device can perform functional assessment upon variable spot optical stimulation of light-activatable biological specimens.

Example 1: FIG. 1A Shows Configuration-1 of OCT Guided Variable Spot stimulation and electrophysiology system. The fiber-coupled visible light sources (1001, 1002, and 1003) were combined with using a Beam Combiner-1 (1004). The light emitted from these sources were used for targeted stimulation of living tissues. A low coherence light from the near infrared imaging source (1005) with center wavelength 860 nm and bandwidth: ~100 nm was combined with Visible light beam using a second Beam Combiner-2 (1006). A Laser isolator (1007) was used to block any back-reflected visible laser beam going into the imaging light source. A fiber-optic 50/50 Beam Splitter (1008) was used to split the imaging light beam to two arms. The beam in the sample arm is guided and scanned using Mirror-1 (1009) and XY MEMS Mirror-2 (1010). The Dynamic Focusing Element (1011, a Liquid lens) in combination with an assembly of Focusing Lenses (1012) was used to focus the imaging and visible laser beams on to the sample. The second beam from the fiber optic Beam Splitter (1008) serves as Reference arm with adjustable path length (1013) consisting of a collimating lens and mirror to back-reflect the reference beam to the Beam Splitter (1008). The back-scattered light from the sample is routed through the assembly of Focusing Lenses (1012), Dynamic Focusing Element (1012), XY MEMS Mirror-2 (1010) and Mirror-1 (1009) to the fiber-optic Beam Splitter (1008), wherein the back-scattered light from the sample was split and collected by a Detector (Spectrometer) (1014). The back-reflected reference beam after splitting at the fiber-optic Beam Splitter (1008) was also collected by the Detector (1014), comprising of a spectrograph-camera. The interference signal between the back-reflected signal from the reference mirror and the back-scattered light signal from the sample is detected with the spectrograph-CCD detector as a function of wavelength. The detected signal (as a function of wavelength) is plotted as a function of wavenumber and then Fourier transformed to obtain optical coherence tomographic (OCT) information, i.e. intensity profile as a function of depth. 3D rendering was carried in a software platform to simplify operation and allow real time adjustment of OCT imaging location and acquisition.

To generate variable-spot(s) targeted stimulation and electrophysiological measurements, user-friendly GUI software was used to control the visible stimulation light beams, NIR imaging beam, OCT-sensor, and acquire imaging/electrophysiological measurements, and perform further processing as well as view the results. Once the measurement spots on the image were identified, the Dynamic Focusing Element (1011, a Liquid lens) was used to control the laser stimulation spot size at each measurement location. The software control panel was used for changing the power and exposure time (scan rate) of the visible laser beams and OCT imaging beam. A Microcontroller (1015) and Computer (1016) with Display (1017) was used to control and automate the visible light sources (1001, 1002, and 1003), low-coherence imaging light source (1005), XY MEMS Mirror-1 & 2 (1009, 1010), the Reference arm with adjustable path length (1013), and the Detector (1014). Electrodes (1018) were used on the sample (eye, brain, retina explant) to measure the electrophysiological activities of tissue while performing 3D image-guided laser stimulation.

The integrated device enabled easy-to-use OCT guided variable spot laser stimulation-based Electroretinography (ERG) and visually evoked potential (VEP, when electrodes are placed in brain/over visual cortex) measurement workflow in one multi-modal platform setting. OCT provided good depth penetration along with excellent depth resolution, and OCT integrated with ERG allowed depth resolved and spatially targeted focal stimulation. ERG measurement provided the electrical responses of various cell types in the retina, including the photoreceptors, inner retinal cells, and the retinal ganglion cells. Various modes of laser stimulation were carried out for different ERG measurements, such as global stimulation, focal stimulation, flickering stimulation, and patterned stimulation to access selective functional information of retina. For measuring label-free opto-elctrophysiology, the phase of the interference signal was measured. Easy-exchangeable imaging lens allowed imaging and irradiation of wide range of species: small (mouse, rat) to large animals (rabbit, pigs/NHP) and human. On the other hand, upon focused illumination of multi-color laser beams, evoked responses in different retinal layers in multiple areas of retina are measured to quickly determine which area of the retina produce abnormal functional response as well as fine navigating the focal stimulation to specific point.

Figure 1B:
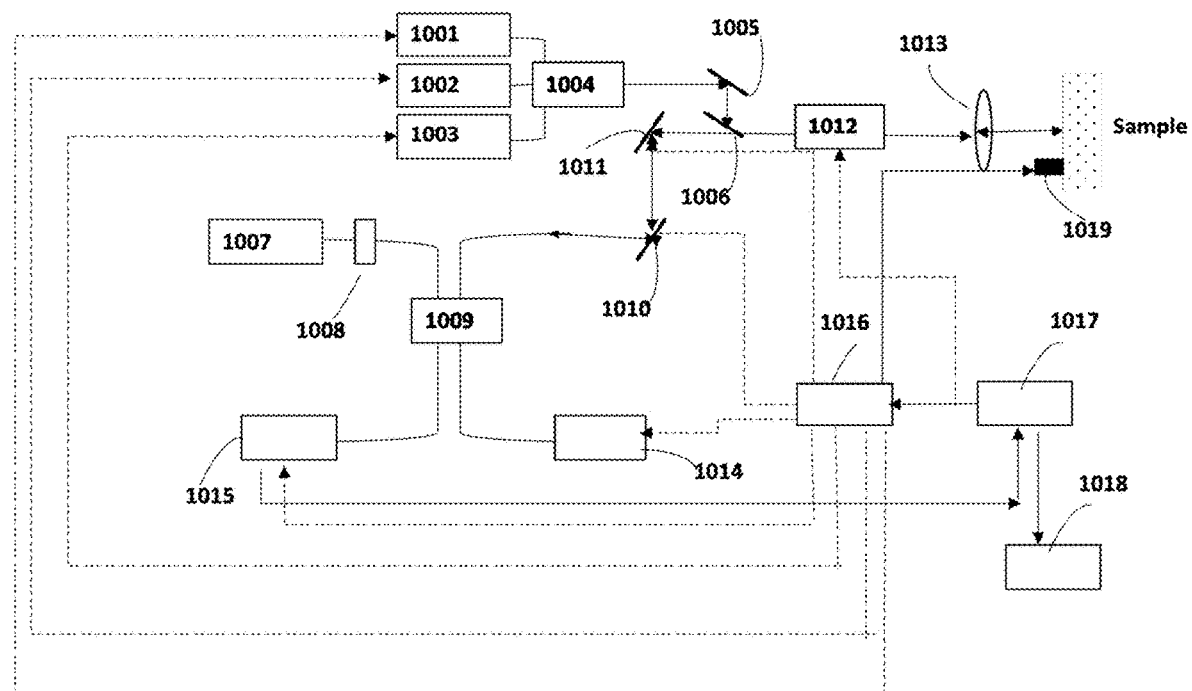
FIG. 1B. Configuration-2 of OCT guided variable spot stimulation and electrophysiology system. 1001: Blue Light Source; 1002: Green Light Source; 1003: Red Light Source; 1004: Beam Combiner-1; 1005: Beam steering optics; 1006: Beam Combiner-2; 1007: Imaging light source; 1008: Laser isolator; 1009: Beam Splitter; 1010: Mirror-1; 1011: Mirror-2; 1012: Dynamic Focusing Element; 1013: Focusing Lens (es); 1014: Reference arm; 1015: Detector; 1016: Microcontroller; 1017: Computer; 1018: Display; 1019: Electrode(s).

Example 2: FIG. 1B shows Configuration-2 of OCT guided variable spot stimulation and electrophysiology system. The visible light sources (1001, 1002, and 1003) were combined in free space with using a Beam Combiner-1 (1004) and guided by a beam stearing optics (1005, XY Mems mirror) to share the identical optical path with the imaging beam. The light emitted from these sources were used for targeted stimulation of living tissues. A low coherence light from the near infrared imaging source (1007) with center wavelength 860 nm and bandwidth: ~100 nm was split into sample beam and reference by a fiber optic 50/50 Beam Splitter (1009) after passing through laser isolator (1008) to black any back-reflected light going into the imaging source. The imaging beam in the sample arm is guided and scanned using Mirror-1 (1010) and XY MEMS Mirror-2 (1011) before combining with the visible stimulation light at dichroic beam combiner (1006). The Dynamic Focusing Element (1012, a Liquid lens) in combination with an assembly of Focusing Lenses (1013) was used to focus the imaging and visible laser beams on to the sample. The second beam from the fiber optic Beam Splitter (1009) serves as Reference arm with adjustable path length (1014) consisting of a collimating lens and mirror to back-reflect the reference beam to the Beam Splitter (1009). The back-scattered light from the sample is routed through the assembly of Focusing Lenses (1013), Dynamic Focusing Element (1012), dichroic beam combiner (1006), XY MEMS Mirror-2 (1011) and Mirror-1 (1010) to the fiber-optic Beam Splitter (1009), wherein the back-scattered light from the sample was split and collected by a Detector (Spectrometer) (1014). The back-reflected reference beam after splitting at the fiber-optic Beam Splitter (1009) was also collected by the Detector (1014), comprising of a spectrograph-camera. The interference signal between the back-reflected signal from the reference mirror and the back-scattered light signal from the sample is detected with the spectrograph-CCD detector as a function of wavelength. The detected signal (as a function of wavelength) is plotted as a function of wavenumber and then Fourier transformed to obtain optical coherence tomographic (OCT) information, i.e. intensity profile as a function of depth. 3D rendering was carried in a software platform to simplify operation and allow real time adjustment of OCT imaging location and acquisition.

To generate variable-spot(s) targeted stimulation and electrophysiological measurements, user-friendly GUI software was used to control the visible stimulation light beams, NIR imaging beam, OCT-sensor, and acquire imaging/electrophysiological measurements, and perform further processing as well as view the results. The dynamic focusing lens was used to maintain focus at multiple depths during imaging. After 3D rendering was carried out, the user was able to change the location and size of stimulation spot size in graphical interface in the software. The scanning mirrors and dynamic focus lens enabled to pin point the exact location based on the 3D rendered image and selected area of stimulation. The software control panel was used for changing the stimulation intensity and number of stimulation repetition of the visible laser beams and OCT imaging beam. To synchronize high speed scanning, dynamic focusing and acquisition hardware, a Microcontroller was used (1016). The computer (1017) with Display (1018) communicates with arduino and to control and automate the visible light sources (1001, 1002, and 1003), low-coherence imaging light source (1007), XY MEMS Mirrors for visible light beam and imaging light beam (1005, 1011), the Reference arm with adjustable path length (1014), and the Detector (1015). Electrodes (1019) were used on the sample (eye, brain, retina explant) to measure the electrophysiological activities of tissue while performing 3D image-guided electrophysiological stimulation.

The integrated device enabled easy-to-use OCT guided variable spot laser stimulation-based Electroretinography (ERG, when electrodes are placed in cornea) and visually evoked potential (VEP, when electrodes are placed in brain/over visual cortex) measurement workflow in one multimodal platform setting. OCT provided good depth penetration along with excellent depth resolution, and OCT integrated with ERG allowed depth resolved and spatially targeted local stimulation. ERG measurement provided the electrical responses of various cell types in the retina, including the photoreceptors, inner retinal cells, and the retinal ganglion cells. Various modes of laser stimulation were carried out for different ERG measurements, such as global stimulation, focal stimulation, flickering stimulation, and patterned stimulation to access selective functional information of retina. For measuring label-free opto-elctrophysiology, the phase of the interference signal was measured. Easy-exchangeable imaging lens (1013) allowed imaging and irradiation of wide range of species: small (mouse, rat) to large animals (rabbit, pigs/NHP) and human. On the other hand, upon focused illumination of multi-color laser beams, evoked responses in different retinal layers in multiple areas of retina are measured to quickly determine which area of the retina produce abnormal functional response as well as fine navigating the focal stimulation to specific point.

Figure 2A:
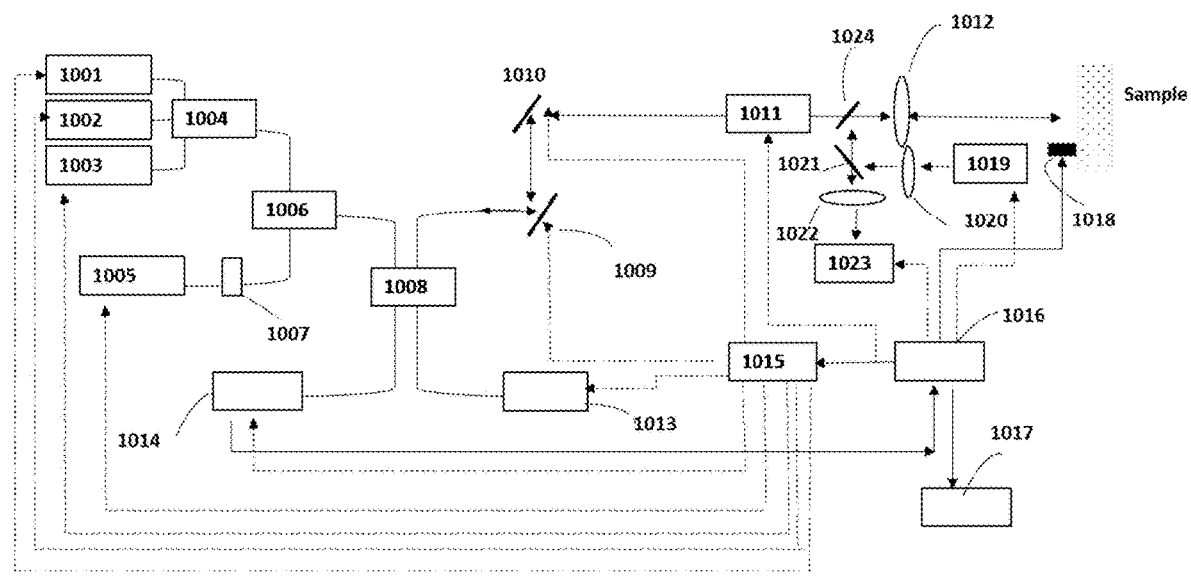
FIG. 2A. Configuration-3 of OCT and Fundus Image guided variable spot stimulation and electrophysiology system. 1001: Blue Light Source; 1002: Green Light Source; 1003: Red Light Source; 1004: Beam Combiner-1; 1005: Imaging light source; 1006: Beam Combiner-2; 1007: Laser isolator; 1008: Beam Splitter; 1009: Mirror-1; 1010: Mirror-2; 1011: Dynamic Focusing Element; 1012: Focusing Lens(es); 1013: Reference arm; 1014: Detector; 1015: Microcontroller; 1016: Computer; 1017: Display; 1018: Electrode(s). 1019: Imaging light source 2; 1020: Collimating optics; 1021: Beam combiner for Imaging optics-2; 1022: Focusing lens(es); 1023: Detector for imaging optics-2; 1024: Beam combiner for imaging modality-2.

Example 3: FIG. 2A shows Configuration-3 of OCT and fundus Image guided variable spot stimulation and electrophysiology system. Most elements in this configuration are identical with configuration 1 in Example 1 except additional components are being added to enable fundoscopic image in addition to OCT image guided variable spot electrophysiology system. In addition to components 1001 to 1018 described in Example 1, second imaging light source (1019) is placed. The illumination light is then focused (1020) and go through the semireflection mirror (1020), then reflected towards the sample by the multi-band optical bandpass filter (1024) to illuminate the sample. The reflected light from the fundus illumination source then travels back the bandpass filter, then pass through the semireflection mirror (1020) before getting focused (1022) into the camera (1023). Although fundoscope does not give any depth penetration like OCT, this configuration enable live fundoscope to enhance the imaging guidance without hindering OCT imaging and electrophysiology capability of the system. The system can detect fluorescence signal from the sample by using visible lasers as illumination source (1001-1003) instead of the second imaging light source (1019). By controlling the xy scanning mirrors (1009, and 1010), point by point scanning and excitation can be realized with selective wavelength (blue, green, red) and the red shifted or blue shifted with broader bandwidth than stimulation source (narrowband 1001-1003) gets reflected by multiband bandpass filter to be acquired in the fundus camera (1023).

Figure 2B:
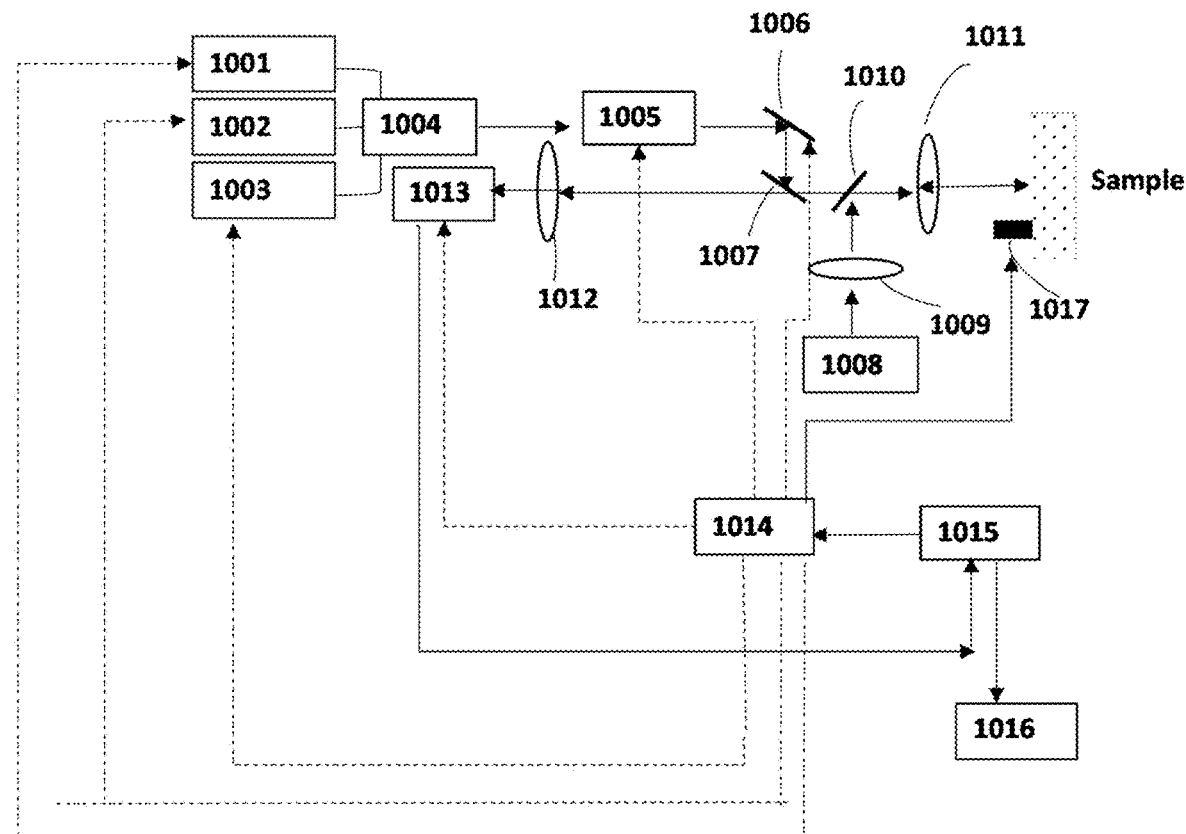
FIG. 2B. Configuration-4 of Fundus Image guided variable spot stimulation and electrophysiology system. 1001: Blue Light Source; 1002: Green Light Source; 1003: Red Light Source; 1004: Beam Combiner-1; 1005: Dynamic focusing element 1; 1006: mirror 1; 1007: mirror-2; 1008: Imaging light source, 1009: Collimating Optics, 1010: Dichroic mirror for imaging light source; 1011: Focusing Lens(es); 1012: Focusing Lens(es); 1013: Detector; 1014: Microcontroller; 1015: Computer; 1016: Display; 1017: Electrode(s).

Example 4: FIG. 2B shows Configuration 4 of Fundus Image guided variable spot stimulation and electrophysiology system. This configuration simplifies the variable spot electrophysiology by allowing fundoscopic imaging to guide the localized stimulation in the sample (eye, brain, retinal explant, other light activable tissue specimen) instead of OCT by giving up depth resolved imaging guidance. The visible light sources (1001, 1002, and 1003) were combined with using a Beam Combiner-1 (1004). The light emitted from these sources were used for targeted stimulation of living tissues. The Dynamic Focusing Element (1005, a Liquid lens) in combination with stearing mirror (1006, MEMS mirror) was used to vary the stimulation spot size and precise location targeting within the imaging field of view. The visible laser beam is then directed to the imaging patch by dichromic mirror (1007). The fundscope imaging light source (1008) is collimated by collimation optics(s) (1009) and reflected toward sample by semireflection mirror (1010), then focused into the sample by focusing optics(s) (1011). The reflected light from the sample then travels back passing the focusing optics(s) (1011), semireflection mirror (1010), dichroic mirror (1017), and focusing optics (1012) before detected by the fundus camera (1013).

Figure 2C:
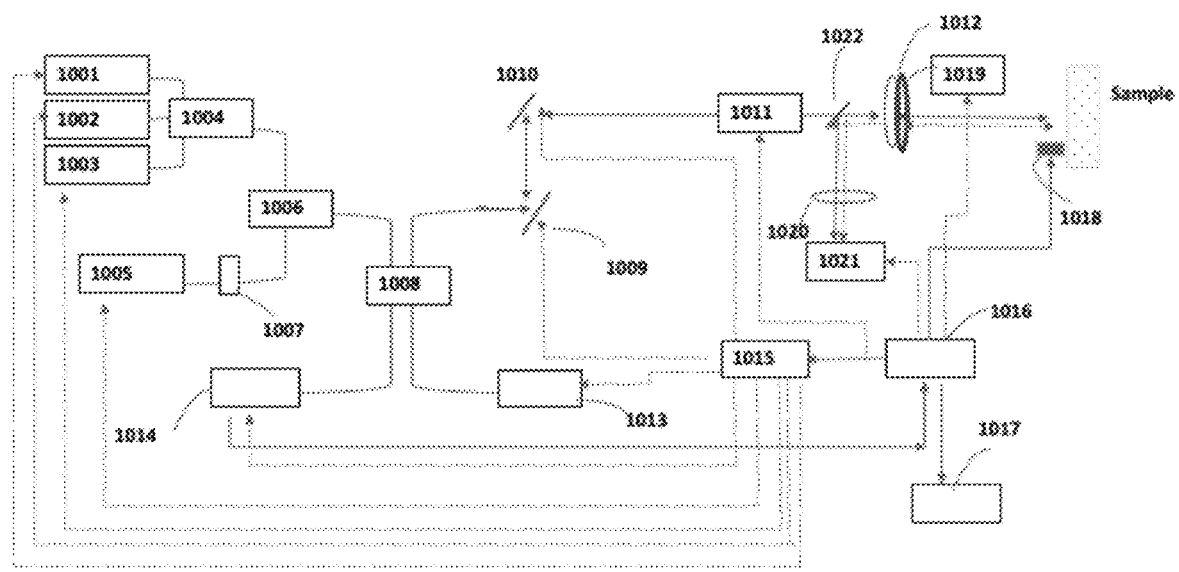
FIG. 2C. Configuration-5 of OCT and Fundus Image guided variable spot stimulation and electrophysiology system. 1001: Blue Light Source; 1002: Green Light Source; 1003: Red Light Source; 1004: Beam Combiner-1; 1005: Imaging light source; 1006: Beam Combiner-2; 1007: Laser isolator; 1008: Beam Splitter; 1009: Mirror-1; 1010: Mirror-2; 1011: Dynamic Focusing Element; 1012: Focusing Lens (es); 1013: Reference arm; 1014: Detector; 1015: Microcontroller; 1016: Computer; 1017: Display; 1018: Electrode(s). 1019: Imaging light source-2 with focusing element; 1020; Focusing lens(es); 1021: Detector for imaging optics-2; 1022; Beam splitter for imaging modality-2.

Example 5: FIG. 2C shows Configuration-5 of OCT and fundus Image guided variable spot stimulation and electrophysiology system. Most elements in this configuration are identical with configuration 3 in Example 3 except the second imaging light source is configured in a ring combined with a focusing element (1019) is placed in front of 1012, the Focusing Lens(es). The reflected light from the fundus then travels back and get routed by the Beam splitter for imaging modality-2 (1022) before getting focused (1020) into the camera (1021). This configuration simplifies the live fundoscopic imaging while allowing OCT imaging and electrophysiology measurements.

To generate variable-spot(s) targeted stimulation and electrophysiological measurements, user-friendly GUI software was used to control the visible stimulation light beams, fundus imaging beam intensity, fundus camera exposure time, and acquire imaging/electrophysiological measurements, and perform further processing as well as view the results. Once the measurement spots on the image were identified, the Dynamic Focusing Element (1005, a Liquid lens) was used to control the laser stimulation spot size at each measurement location. A Microcontroller (1014) and Computer (1015) with Display (1016) were used to control and automate the visible light sources (1001, 1002, and 1003), MEMS Mirror (1006), and the fundus Detector (1013). Electrodes (1017) were used on the sample (eye, brain, retina explant) to measure the electrophysiological activities of tissue while performing image-guided laser stimulation.

The integrated device enabled simple fundoscopy image guided variable spot laser stimulation-based Electroretinography (ERG) and visually evoked potential (VEP, when electrodes are placed in brain/over visual cortex) measurement workflow in one multi-modal platform setting. ERG measurement provided the electrical responses of various cell types in the retina, including the photoreceptors, inner retinal cells, and the retinal ganglion cells. Various modes of laser stimulation were carried out for different ERG measurements, such as global stimulation, focal stimulation, flickering stimulation, and patterned stimulation to access selective functional information of retina. Easy-exchangeable imaging lens allowed imaging and irradiation of wide range of species: small (mouse, rat) to large animals (rabbit, pigs/NHP) and human. On the other hand, upon focused illumination of multi-color laser beams, evoked responses in different retinal layers in multiple areas of retina are measured to quickly determine which area of the retina produce abnormal functional response as well as fine navigating the focal stimulation to specific point.

Figure 3A:
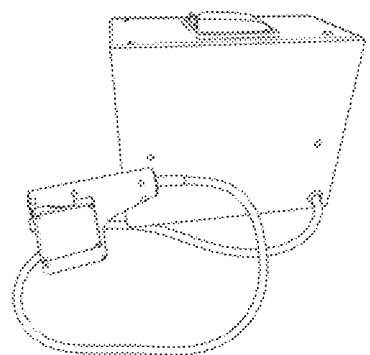
FIG. 3A. OCT guided ERG system chassis with a scanner head.
Figure 3B:
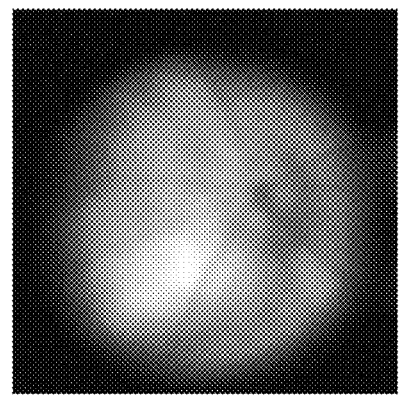
FIG. 3B. Live fundus image of a rodent retina (Rat).
Figure 3C:
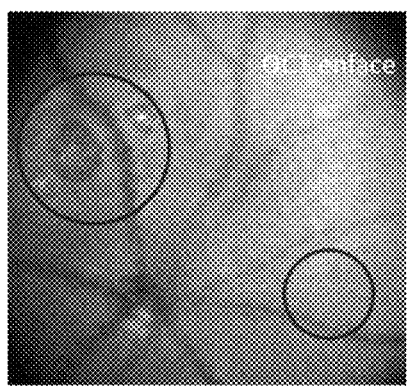
FIG. 3C. OCT enface (i.e En-face or En face) recreation from 3D OCT imaging. The marked circle represents the area of ERG stimulation for diagnosis. Localized, various sizing stimulation is achieved with the modality.
Figure 3D:
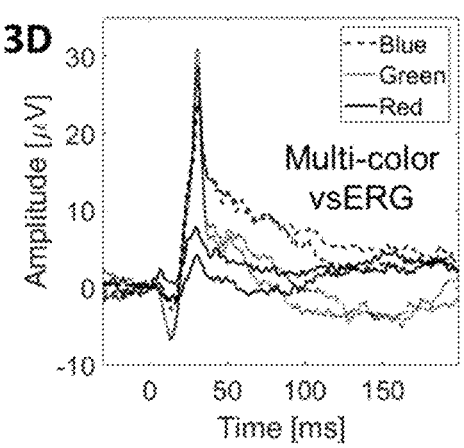
FIG. 3D. Multicolor ERG profile showing different response from blue, green, and red stimulation for different cones (S, M and L) function assessment.

Example 5: FIG. 3A shows OCT guided variable ERG system chassis with a scanner head. Live fundus image of a rodent retina (Rat) is shown in FIG. 3B. FIG. 3C shows OCT enface recreation from 3D OCT imaging. The marked circle represents area of ERG stimulation for diagnosis. Localized, various sizing stimulation is realized with the modality. FIG. 3D depicts multicolor ERG functional assessment profiles showing different response upon blue, green, and red stimulation for different cones (S, and M) of wild type mice (C57BL/6J). Different ERG profile using multicolor stimulation shows the different compound response from individual photoreceptors and higher order neurons. Since mouse does not have L cones, the ERG response with red stimulation was minimum, and S-cones show broadened response (Blue light stimulation) compared to M-cones (Green light stimulation).

To simplify the fundus imaging integrated with OCT and electrophysiology measurements, light sources (LEDs) are configured in a ring fashion to illuminate the eye.

Figure 3E:
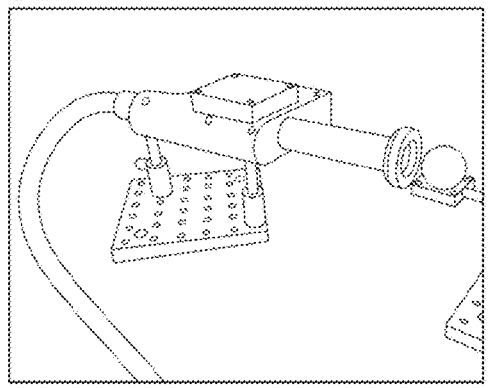
FIG. 3E. OCT guided ERG system scanner head with fundus imaging light source, imaging the model eye (white globe, on the right).
Figure 3F:
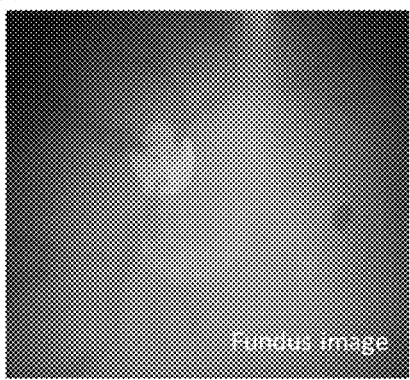
FIG. 3F. Fundus image of a model eye, showing black curve features mimicking the blood vessels. The white patch simulates the optic nerve.
Figure 3G:
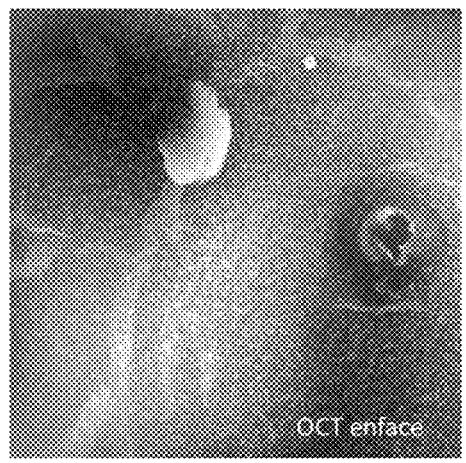
FIG. 3G. OCT enface image of a model eye, showing black curve features mimicking the blood vessels. The white patch simulates the optic nerve.

FIG. 3E shows the OCT guided ERG system scanner head with fundus imaging light source, imaging the model eye (white globe, on the right). The Fundus image of a model eye is shown in FIG. 3F, wherein the black curve features mimicking the blood vessels. The white patch in the model eye fundus image simulates the optic nerve. FIG. 3G depicts the OCT enface image of the model eye, showing black curve features mimicking the blood vessels. The white patch simulates the optic nerve.

Figure 4:
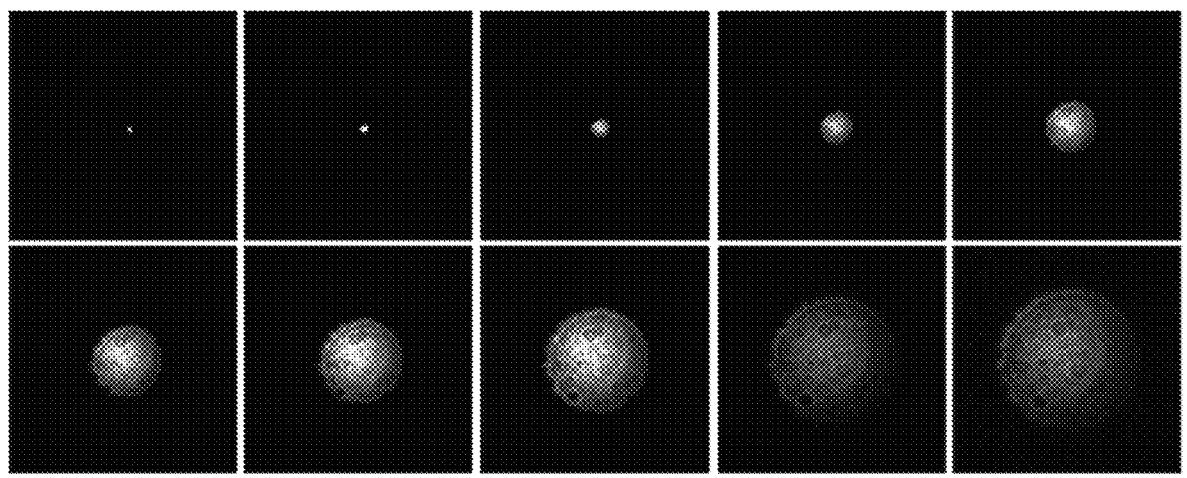
FIG. 4. Stimulation spot size variation control with focusing element. The steering optics realize precise localization of the stimulation, and focusing element can vary stimulating spot size from focused spot to field of view.

Example 6: FIG. 4 shows how the dynamic focusing element can be used for varying the stimulation spot size. The steering optics enables precise localization of the stimulation spots co-registered with image generated by OCT and/or fundoscopic imaging. The focusing element can vary stimulating spot size from micro-focused spot to large spot covering the field of view. The field of view of the imaging system varies from small rodent systems (mouse and rat) to large animal systems (rabbit, pig, and NHP) and clinical systems. The dynamic focusing lens allows tight focus at the sample plan for higher spatial resolution for imaging and can be varied to fill the aperture of the focusing objective lens to stimulate entire imaging field of view.

Figure 5A:
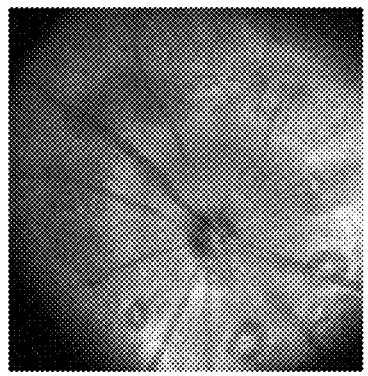
FIG. 5A. Determination of spatial resolution of vsERG. Enface OCT image after OCT-guided targeted laser micro irradiation (Peripheral retinal degeneration model).
Figure 5B:
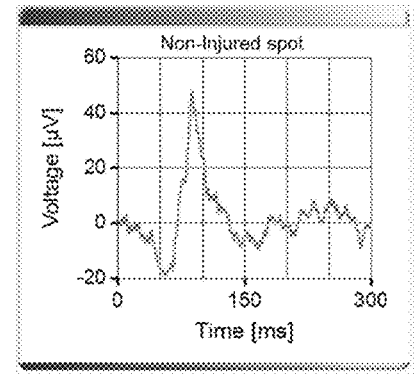
FIG. 5B. ERG response of non-injured site.
Figure 5C:
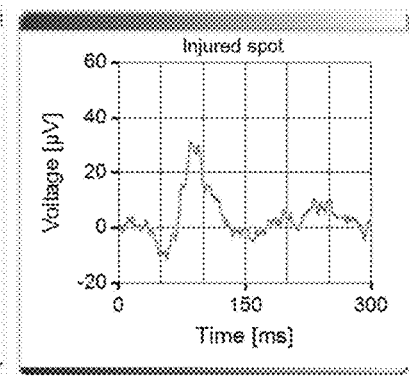
FIG. 5C. ERG response of injured site showing decrease in ERG amplitude in injured site.

Example 7: Determination of spatial resolution of variable spot OCT guided ERG system was carried out experimentally. Instead of using stimulation laser, lasers with the same specification as the stimulation laser but higher power was coupled to the variable spot OCT guided ERG system. Then dynamic focusing element was varied to irradiate a mouse retina in different spot sizes to generate local tissue damage to visualize precision and localization of the laser stimulation. The OCT guided laser microirradiation integrated electrophysiology system was used to measure functional deficits in the Dry-AMD mouse model created by OCT-guided Laser injury, was measured by integrated variable spot ERG. FIG. 5A shows enface (OCT) image of laser-treated retina showing injured spots in peripheral retina. OCT-guided visual illumination over a range of intensities was presented separately to measure activities in control regions as well as laser-injured regions. Scotopic variable-spot Electroretinography (vsERG) response from the uninjured retina region showing typical ERG response is shown in FIG. 5B. Scotopic vsERG response from the laser-damaged region exhibited diminished ERG response, as shown in FIG. 5C. The spatial resolution of vsERG measurement was determined to be ~0.05 mm.

To further determine the accuracy of OCT-guided variable spot ERG system, pig model of geographic atrophy was created using laser injury. The B-scan and immunostaining images showed localized outer nuclear layer damage with the laser injury wherein the photoreceptor layer as well as RPE layer is abolished without inner retina damage. The vsERG signals between normal and abnormal (laser-injured) regions within the same retina were carried out. OCT guided vsERG measurements in a healthy pig retina outside of the laser-injury region show response the blue light vsERG response, but no ERG signal response using red stimulation (as pigs lack L-cones). However, when the retinal area inside of laser-injured region was selected for the same stimulation parameters (stimulation spot size, wavelength, and intensity), no response was detected while using blue or red-light stimulation. These experiments demonstrated that OCT-guided vsERG can not only enable establishment of structure-function relationship in partially atrophic retina in a spatially resolved manner, but it can also distinguish subtle changes occurring in retina in near-real-time (minutes of laser injury).

Figure 6A:
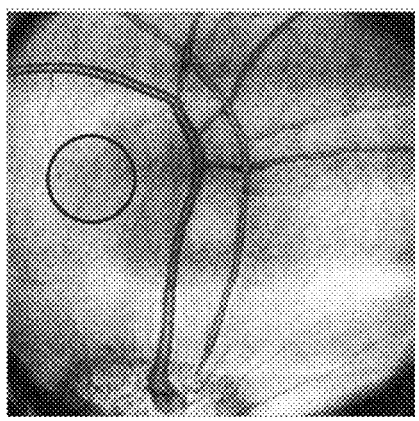
FIG. 6A. Assessment of regional function using OCT-guided variable spot ERG measurements with scaled ISCEV standard protocols. Standard cone ERG protocol with 2 mm stimulation spot (3 cd·s/m$^2$ stimulation under light adaptation).
Figure 6A:
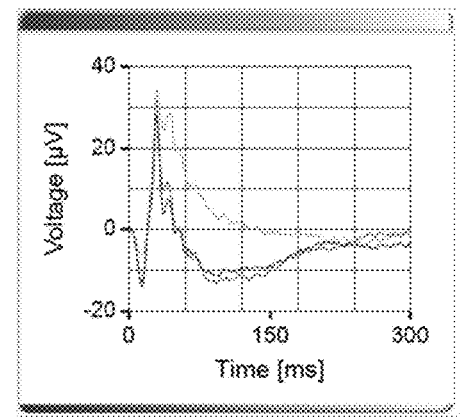
Figure 6B:
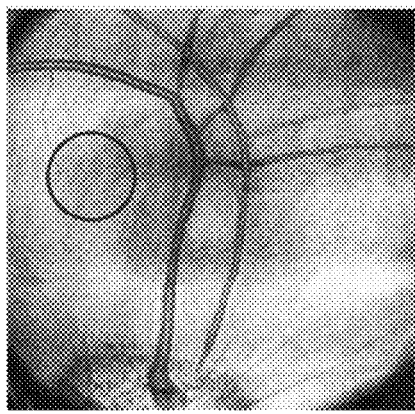
FIG. 6B. Standard rod and cone ERG protocol with 2 mm stimulation spot (3 cd·s/m$^2$ under dark adaptation).
Figure 6B:
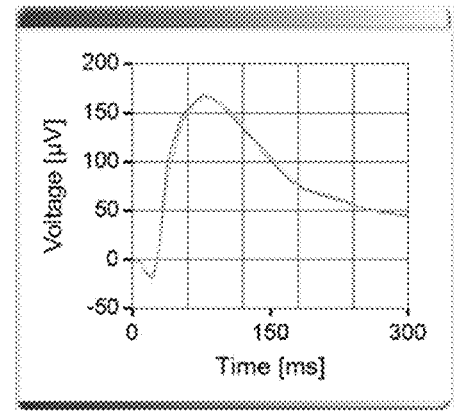
Figure 6C:
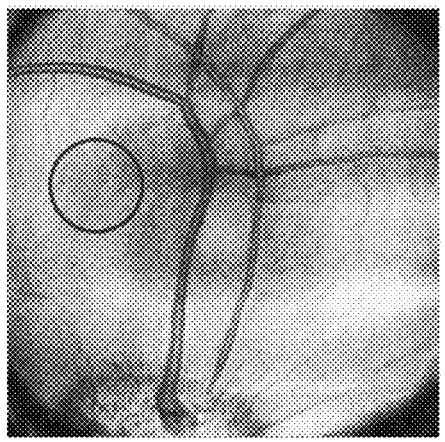
FIG. 6C. Scotopic rod ERG protocol with 2 mm stimulation spot (0.01 cd·s/m$^2$ under dark adaptation).
Figure 6C:
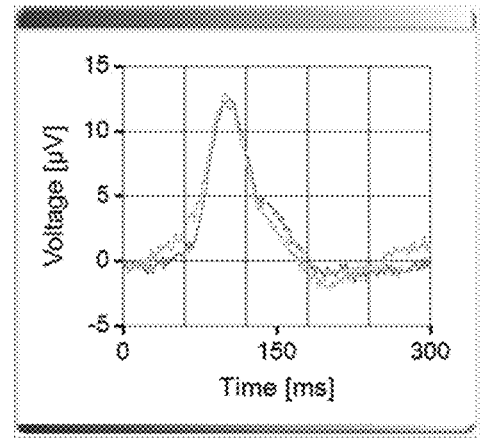
Figure 6D:
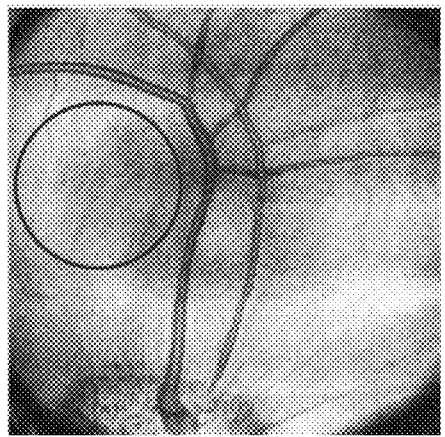
FIG. 6D. Identical scotopic rod ERG protocol with 4 mm stimulation spot showing stimulation size dependent response.
Figure 6D:
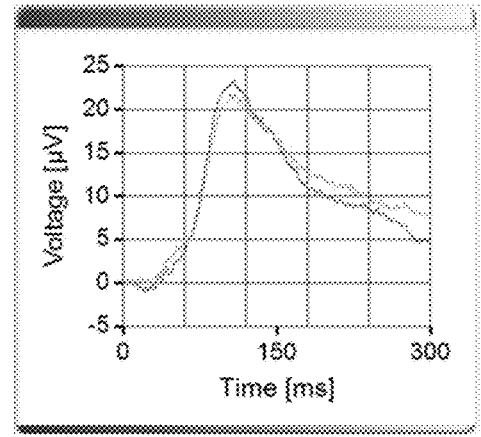

Example 8: There often is a need to measure function from specific or multiple retinal cell types to evaluate disease progression or assessing the therapeutic outcome. For example, in contrast to inherited retinal degenerative diseases and dry-AMD where photoreceptor and RPE damage occurs, Glaucoma is associated with damage to RGCs. For evaluating pathological progression of GA, or development of new atrophies, OCT guided spatiotemporal control of electrophysiological evaluation provides unique opportunity. Further, while Retinitis Pigmentosa is associated with loss of rods preceding loss of cones, in case of cone-rod dystrophy loss of cones leads to loss of rods. By varying the wavelength of the OCT-guided visible laser stimulation beam of controllable spot size allowed selective functional evaluation of rods vs. specific (S, M, L) cones. FIG. 6A shows assessment of regional function using OCT-guided variable spot ERG measurements with scaled ISCEV standard protocols. Standard cone ERG protocol with 2 mm stimulation spot (3 cd·s/m$^2$ stimulation under light adaptation) showing color dependent response. FIG. 6B shows Standard rod and cone ERG protocol with 2 mm stimulation spot (3 cd·s/m$^2$ under dark adaptation). FIG. 6C shows Scotopic rod ERG protocol with 2 mm stimulation spot (0.01 cd·s/m$^2$ under dark adaptation). FIG. 6D shows Identical scotopic rod ERG protocol with 4 mm stimulation spot showing stimulation size dependent response.

Figure 7A:
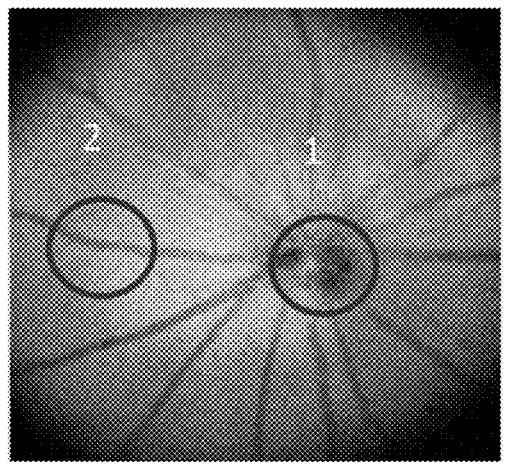
FIG. 7A. OCT guided variable spot visually evoked potential (VEP) measurements. OCT enface showing two different locations of stimulation.
Figure 7B:
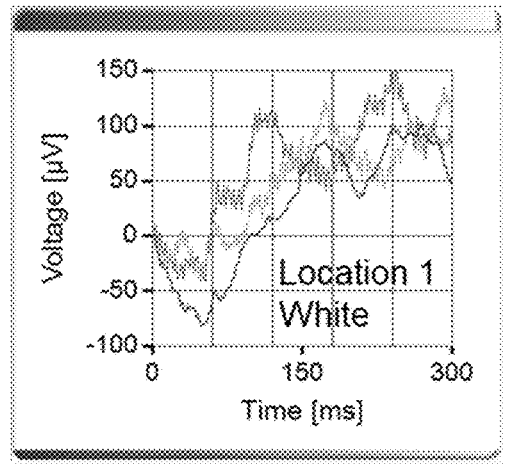
FIG. 7B. VEP measured in visual cortex with white light stimulation at location 1.
Figure 7C:
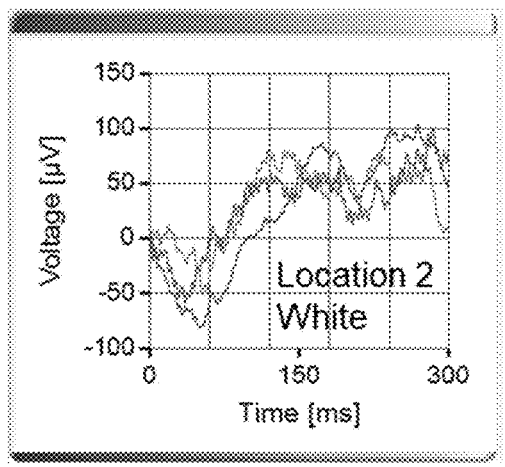
FIG. 7C. VEP measured in visual cortex with white light stimulation at location 2. VEP response from optic nerve region (location 1) shows lower response.
Figure 7D:
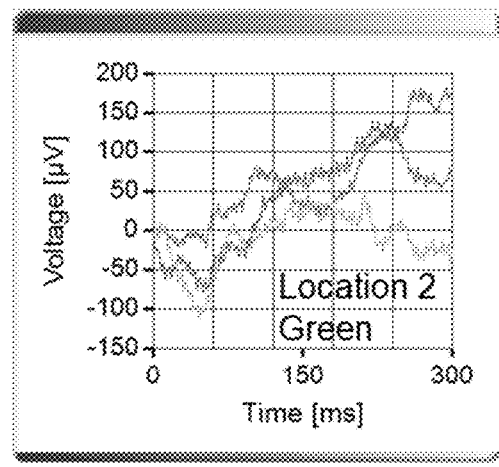
FIG. 7D. VEP measured in visual cortex with green light stimulation at location 2 shows higher response compared to that of white light stimulation.

Example 9: The OCT guided variable spot electrophysiology system is not limited to measure localized electroretinogram in retina, but is used to measure visually evoked potential (VEP, when electrodes are placed in brain/over visual cortex) emerging from localized stimulation. FIG. 7A shows OCT enface showing two different locations of stimulation in rodent retina for OCT guided variable spot VEP measurements. FIG. 7B shows VEP measured in visual cortex with white light stimulation at location 1. FIG. 7C shows VEP measured in visual cortex with white light stimulation at location 2. VEP response from optic nerve region (location 1) shows lower response. FIG. 7D shows VEP measured in visual cortex with green light stimulation at location 2 shows higher response compared to that of white light stimulation with equal stimulation intensity.

Figure 8A:
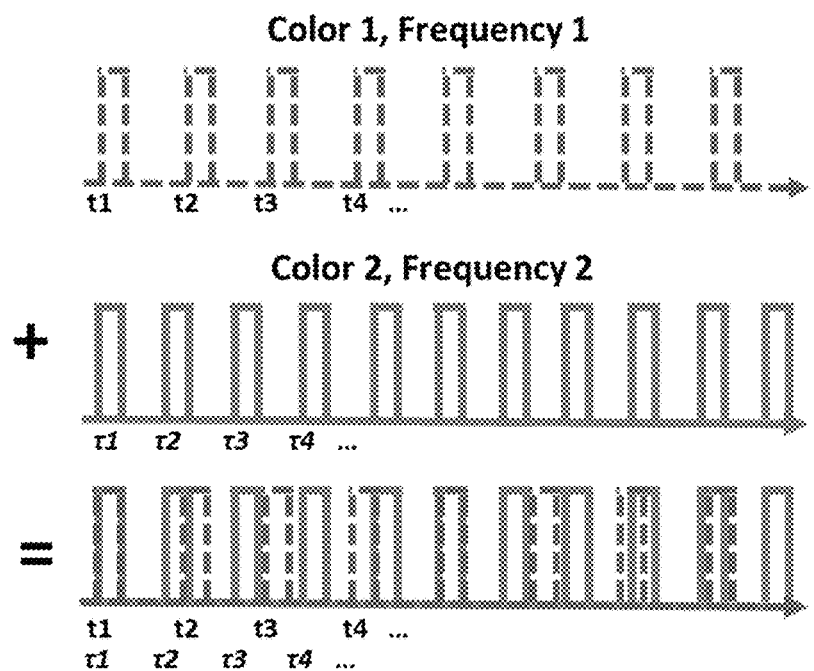
FIG. 8A. Multiplexing stimulation scheme for simultaneous detection of different photoreceptor response using multiplexing wavelength and frequency. Time stamps for color 1 (frequency 1) light pulses are denoted by t1, t2 . . . and that for color 2 (frequency 2) light pulses are denoted by $\Sigma$1, $\tau$2 . . . .
Figure 8B:
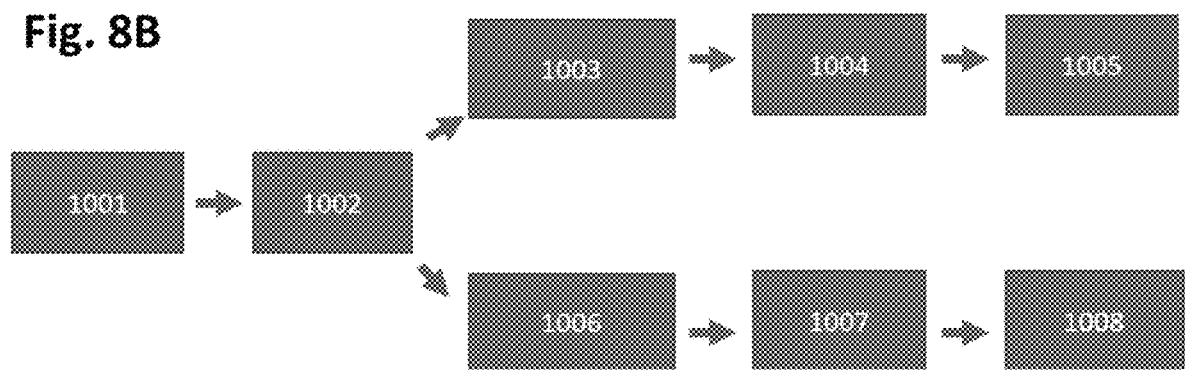
FIG. 8B. Decoupling different cone responses based on frequency response using Fourier domain frequency filtering. 1001: Signal acquisition; 1002: Frequency bandpass filter; 1003: Averaging with respective to color 1 time stamps (t1, t2, t3 . . . ); 1004: Frequency 1 signal extraction; 1005: Response of photoreceptor type 1; 1006: Averaging with respective to color 2 time stamps ($\tau$1, $\tau$2, $\tau$3 . . . ); 1007: Frequency 2 signal extraction; 1008: Response of photoreceptor type 2.
Figure 8C:
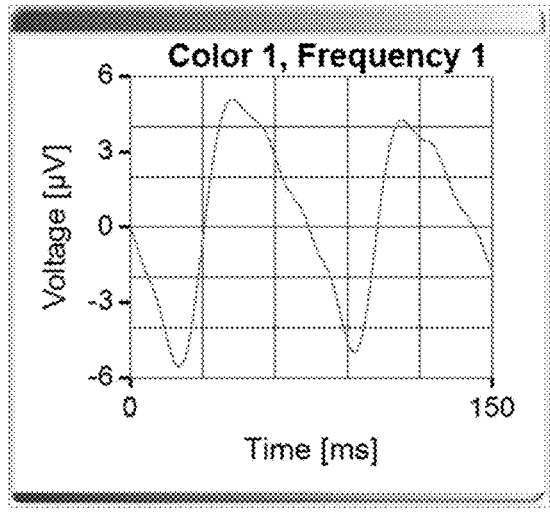
FIG. 8C. Flicker ERG response using 14 Hz red stimulation.
Figure 8D:
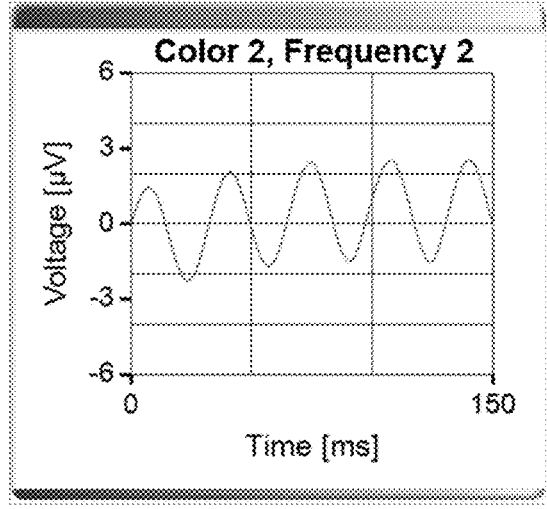
FIG. 8D. Flicker ERG response using 31 Hz blue stimulation at the same location.
Figure 8E:
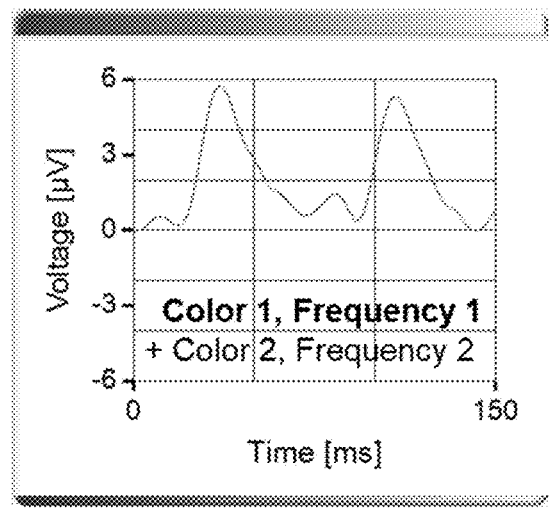
FIG. 8E. Flicker ERG response using linear combination of red at 14 Hz, and blue at 31 Hz when averaged with red light stimulation time stamps.
Figure 8F:
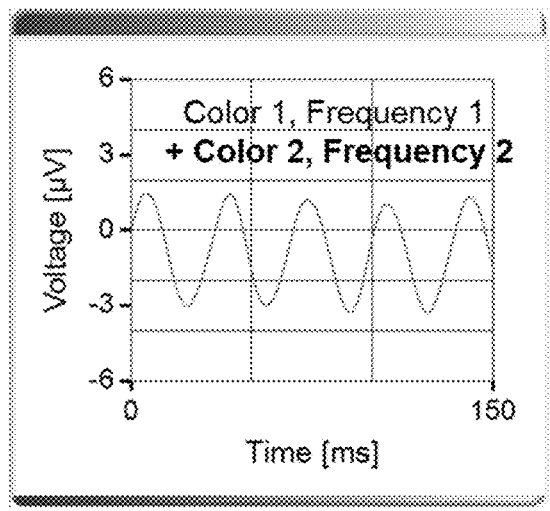
FIG. 8F. Flicker ERG response using linear combination of red at 14 Hz, and blue at 31 Hz when averaged with blue light stimulation time stamps.

Example 10: For flicker stimulation which uses certain set of frequency pulse train stimulation within given window, multiple color stimulation can be combined to measure individual color responses from the identical area with single stimulation pulse train by frequency multiplexing. Since different type of photoreceptors have a different absorption profile as function of wavelength, when different types of photoreceptors are stimulated with combination of multiple color stimulation with distinct frequency, individual photoreceptors only respond to the matching color stimulation at the stimulated frequency. FIG. 8A shows frequency multiplexing stimulation scheme for simultaneous detection of different cone response. Top pulse train illustrates blue light flicker stimulation intensity profile as function of time, and middle pulse train illustrates red light flicker stimulation at slightly faster frequency repetition rate. t1, t2, t3 represent the time stamp for color 1 stimulation pulse train and $\tau 1, \tau 2, \tau 3$ represent the time stamp for color 2 stimulation. The bottom pulse train shows linear combination of the blue flicker stimulation and red stimulation train super imposed on top of each other. This mixed single pulse train sequence can be used to detect photoreceptors response from blue light and red-light stimulation simultaneously. FIG. 8B shows method for decoupling of different photoreceptor responses based on frequency response using Fourier domain frequency filtering. Synchronized averaging (1003) of the filtered acquired signal with respective to color 1 time stamps (t1, t2, t3 . . . ) extracts frequency 1 signal (1004) while reducing other frequency signal component. This extracted signal represents response of photoreceptor type 1 (1005) which is color and frequency dependent. Similarly, synchronized averaging (1006) of the filtered acquired signal with respective to color 2 time stamps ($\tau 1$, $\tau 2, \tau 3$ . . . ) extracts frequency 2 signal (1007) while reducing other frequency signal component(s). This extracted signal represents response of photoreceptor type 2 (1008). FIG. 8C shows flicker ERG response using red, and 14 Hz stimulation and FIG. 8D. shows flicker ERG response using blue, and 31 Hz stimulation at the same location. FIG. 8E demonstrates flicker ERG response using linear combination of red at 14 Hz, and blue at 31 Hz when averaged with red light stimulation time stamps while FIG. 8F shows Flicker ERG response using linear combination of red at 14 Hz, and blue at 31 Hz when averaged with blue light stimulation time stamps.

Figure 9:
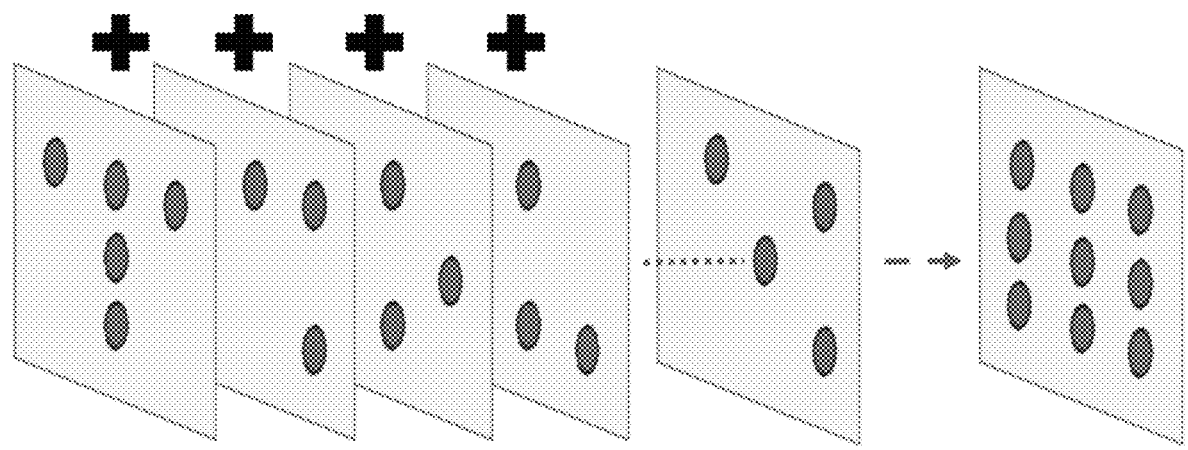
FIG. 9. Spatial-temporal stimulation schematic to increase signal to noise ratio. For multi-location stimulations, about half of random locations are simulated at a given time and local response from individual locations can be extracted from linear combination of the stimulation, thus increasing SNR per stimulation by averaging compared to single location stimulation.

Example 11: For electrophysiological signal that has a temporally delayed/long lasting profile, spatial-temporal stimulation multiplexing can be utilized to increase signal to noise ratio (SNR) of averaged signal by stimulating multiple locations simultaneously compared to sequentially stimulating single position at a time. This method is widely used in multi focal ERG to reduce total acquisition time and increase signal to noise ratio per stimulation. FIG. 9 Illustrates spatial-temporal stimulation schematic to increase signal to noise ratio. For multi-location stimulations, about half of random locations are simulated at a given time and local response from individual location can be extracted from linear combination of the stimulation, thus increasing SNR per stimulation by averaging compared to single location stimulation.

Figure 10A:
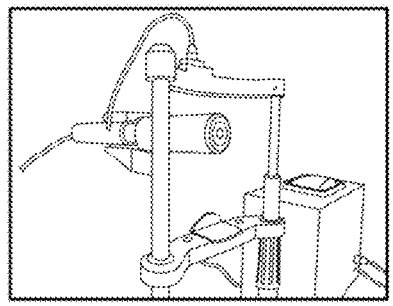
FIG. 10A. Integrated OCT guided ERG scanner for simultaneous assessment.
Figure 10B:
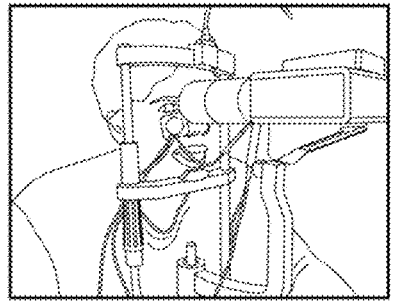
FIG. 10B. Experimental setup of OCT-guided variable spot ERG system for clinical studies.

Example 12: FIG. 10A shows integrated OCT guided variable spot electrophysiology platform for clinical studies. The PC and all hardware are enclosed in the compact system chassis to facilitate office use in clinics. The adjustable LED light attached to the chin rest serves as fixation target during examination. FIG. 10B illustrates experimental setup of OCT-guided variable spot ERG system with electrodes connected (Signal electrode on cornea, reference electrode below the eye, and ground electrode placed on forehead). The chin rest provides stability to the patient and the scanner is attached to the chin rest with translational and rotational adjustment capabilities.

Figure 10C:
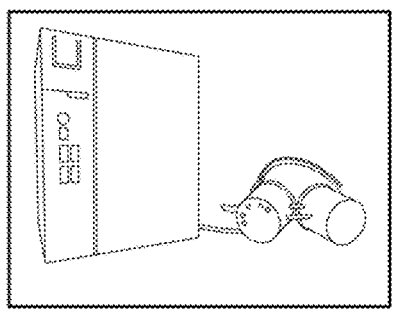
FIG. 10C. Integrated OCT guided wearable ERG system.
Figure 10D:
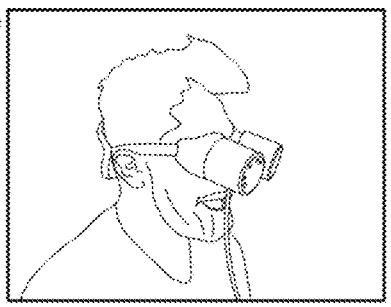
FIG. 10D. Experimental setup of OCT guided variable spot size ERG goggles system.

FIG. 10C shows integrated wearable OCT guided variable spot electrophysiology goggles for clinical studies. The separated binocular configuration allows independent ERG stimulation of each eye for electrophysiology measurement. Finally, FIG. 10D illustrates a setup of the OCT-guided wearable variable spot ERG Goggle. The wearable goggles ERG platform further reduces motion artifact for localized ERG stimulation since any motion of the body or head is canceled by the wearable goggles.

Figure 11A:
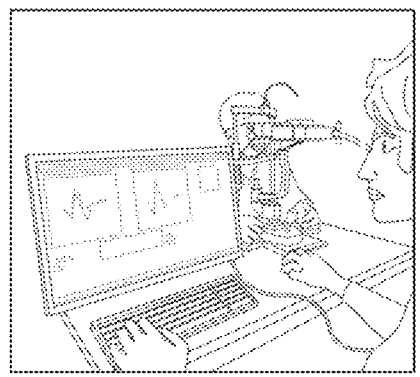
FIG. 11A. OCT-guided variable spot ERG system for clinical studies.
Figure 11B:
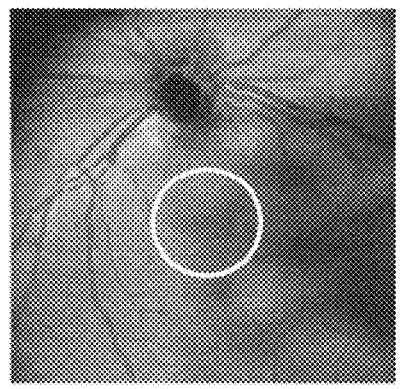
FIG. 11B. Enface OCT image with 2 mm spot size stimulation.
Figure 11C:
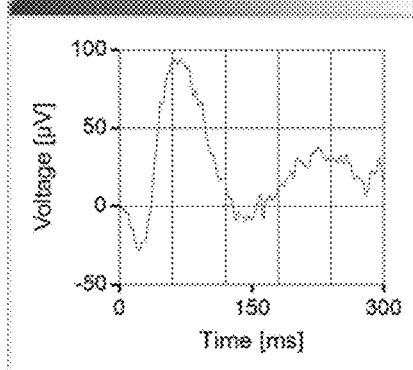
FIG. 11C. Standard cone ERG measurement.
Figure 11D:
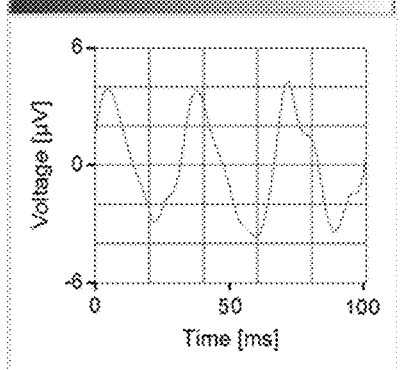
FIG. 11D. 30 Hz flicker ERG measurement.

Example 13: FIG. 11A shows example of clinical setup during OCT-guided variable spot ERG measurement. First, OCT images are acquired to access depth resolved structural information of the retina. Based on structural assessment, the user can graphically overlay the stimulation location and adjust size of stimulation area in the enface image, along with other stimulation parameters. FIG. 11B shows an example of enface OCT image. With 2 mm spot size stimulation, variable spot ERG profile was measured using Standard cone ERG protocol (FIG. 11C) and 30 Hz flicker ERG protocol (FIG. 11D).

Figure 11E:
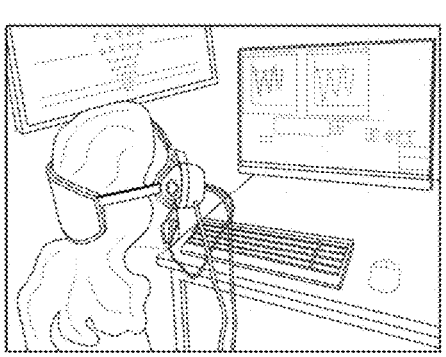
FIG. 11E. OCT-guided wearable variable spot ERG system for clinical studies.
Figure 11F:
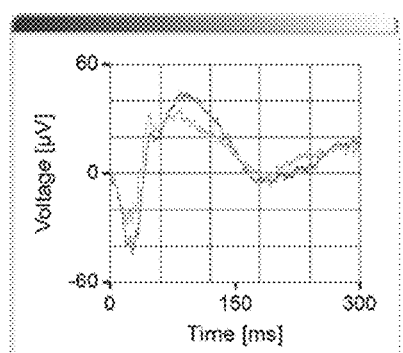
FIG. 11F. Standard rod cone ERG measurement with the OCT guided variable spot size ERG FIG. 12. OCT-guided variable spot ERG system software interface for clinical trial. Left panel shows individual measurements, and middle panel shows the average signal. The top right most images show OCT enface and cross sections of the stimulation area (Marked dark circle with white cross lines).

FIG. 11E illustrates an example of a clinical setup during the OCT-guided variable spot ERG measurement with the wearable goggles. Similar to benchtop system, the structural assessment of the retina is performed, followed by ERG stimulation area defined by user. The wearable goggles-based image-guided ERG system allows dark adaptation with the room light on due to complete blockage of the ambient light by the goggles. For photopic measurements, background light is turned on within the goggles, in a controlled manner. With the goggles blocking the ambient light and nearby activity, the goggles setup allows significant reduction of noise and help to ensure consistent measurements.

Figure 12:
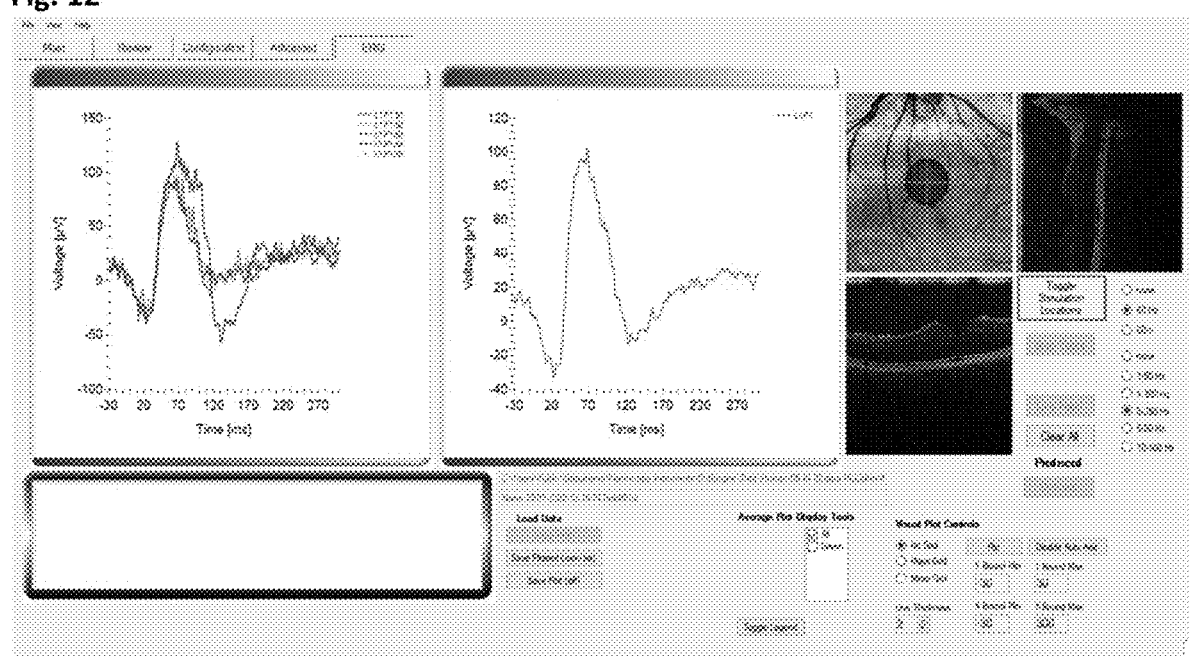

Example 14: FIG. 12 shows OCT-guided variable spot ERG system software interface for clinical trial. Left panel shows individual measurement using standard cone ERG protocol, and middle panel shows the average signal. The OCT enface image is shown on top and marked black circle indicates the area of stimulation. The white cross lines show xy cross sections which are displayed in the right and bottom OCT B-scan images. The user can digitally control measurement parameters such as color of stimulation, mode of stimulation (different ISCEV protocols) and number of stimulations to be averaged in the software as well as can process data and view the results. The software offers different filtering, averaging method, and all the data can be saved, loaded, and processed again.

Figure 13A:
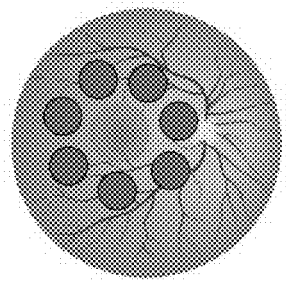
FIG. 13A. Peripheral measurement using ring pattern. Multiple stimulation pattern scheme generated by OCT guided variable spot ERG.
Figure 13B:
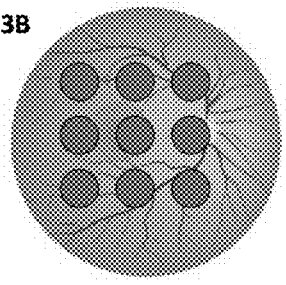
FIG. 13B. Linear square pattern for OCT guided variable spot ERG measurements.
Figure 13C:
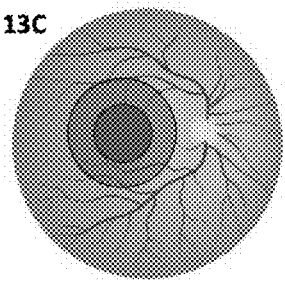
FIG. 13C. Concentric pattern for OCT guided variable spot ERG measurements.
Figure 13D:
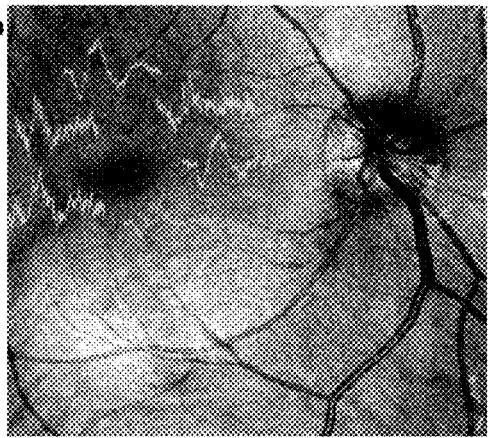
FIG. 13D. ERG response measurement overlayed using peripheral ring pattern (NHP).
Figure 13E:
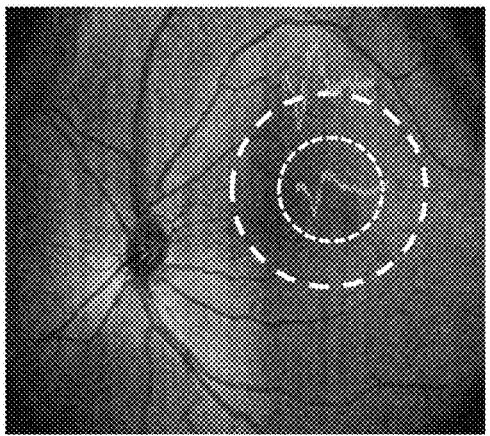
FIG. 13E. ERG response measurement overlayed using concentric pattern (Human).

Example 15: With freedom of precisely locating electrophysiology stimulation anywhere within the field of view of imaging modality, different stimulation pattern can be used to access the functional response of multiple regions of interest. FIG. 13A shows peripheral stimulation using a ring pattern surrounding macular region and FIG. 13B shows linear square pattern for OCT guided variable spot ERG measurements. FIG. 13C shows concentric pattern measurement scheme which implements changing of the stimulation spot size at the same location without changing the stimulation location. By measuring the different concentric spot size electrophysiological response, and subtracting response of smaller area from the response from the larger area, peripheral response excluding the central response can be calculated. FIG. 13D illustrates ERG response measurement overlayed using peripheral ring pattern (NHP). FIG. 13E shows ERG response measurement overlayed using concentric pattern (Human) in the software after analysis.

We were able to acquire 3D volumetric OCT scan and navigate within the acquired volume to target the region of interest, while the cross-sectional OCT scan displayed. After stimulation spot is selected, the software prompts which two depths should be selected for phase difference measurement. Once the two depths of interest are determined, stationary OCT signal over time (M-scan) starts generating computed phase change and display in separate window with default B-scan frame rate. Finally, when the stimulation option is initiated with set pulse width and repetition rate, the interactive software provide insight about the stimulation status such as: (i) potential damage from bulk heating effect; and (ii) power adjust suggestions based on overall phase change calculation. The user-friendly GUI software provides a platform for user interaction, allowing the user to control the OCT image acquisition in multiple scanning mode: A-scan functional probing, B&C-scan for structural imaging for identifying stimulation location. The software allows navigation through the region of interest within OCT scan by adjustable scanning range and depth of focus. Within the same OCT software platform, the users have access to a control panel for customizing the stimulation laser such as power, pulse duration, frequency of stimulation and specific ROI selection within the OCT scan. When the stimulation-option is initiated, it prompts the user with a list of parameters and will guide the user through the delivery process. Thus, the integrated device and software provides 3D OCT image guided micro-focused laser stimulation control and temperature measurement. The software also provides easy analysis of raw M-scan data for probing functional (neural activities) changes by measuring phase OCT signal either offline or online.

The specification and examples herein provide a complete description of the structure and use of illustrative embodiments. Although certain embodiments have been described with a certain degree of particularity, or with reference to one or more individual embodiments, those skilled in the art could make numerous alterations to the disclosed embodiments without departing from the scope of this invention. As such, the various illustrative embodiments of the devices are not intended to be limited to the particular forms disclosed. Rather, they include all modifications and alternatives falling within the scope of the claims, and embodiments other than the one shown may include some or all of the features of the depicted embodiment. For example, components may be omitted or combined as a unitary structure, and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

While the device, compositions and methods of this invention have been described in terms of preferred embodiments, it will be apparent to those of skill in the art that variations may be applied to the device, compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be realized. All such similar substitutes and modifications apparent to those skilled in the art are deemed to be within the spirit, scope and concept of the present invention.

Furthermore, the claims are not intended to include, and should not be interpreted to include, means-plus- or step-plus-function limitations, unless such a limitation is explicitly recited in a given claim using the phrase(s) "means for" or "step for," respectively.

REFERENCES

The following references, to the extent that they provide exemplary procedural or other details supplementary to those set forth above, are specifically incorporated by reference.

ADDIN EN.REFLIST 1. Lim, L. S., Mitchell, P., Seddon, J. M., Holz, F. G. & Wong, T. Y. Age-related macular degeneration. *The Lancet* 379, 1728-1738 (2012).
2. Swain, P. K., et al. Mutations in the cone-rod homeobox gene are associated with the cone-rod dystrophy photoreceptor degeneration. *Neuron* 19, 1329-1336 (1997).
3. Perrault, I., et al. Leber congenital amaurosis. *Molecular genetics and metabolism* 68, 200-208 (1999).
4. Kalatzis, V., Hamel, C. P., MacDonald, I. M. & Symposium, F. I. C. R. Choroideremia: towards a therapy. *American journal of ophthalmology* 156, 433-437. e433 (2013).
5. Sandberg, M. A., Jacobson, S. G. & Berson, E. L. Foveal cone electroretinograms in retinitis pigmentosa and juvenile macular degeneration. *American journal of ophthalmology* 88, 702-707 (1979).
6. Han, Z., Conley, S. M. & Naash, M. I. Gene therapy for Stargardt disease associated with ABCA4 gene. *Adv Exp Med Biol* 801, 719-724 (2014).
7. Oh, K. T., et al. Electroretinographic findings in patients with Stargardt disease and fundus flavimaculatus. *Retina* 24, 920-928 (2004).
8. Hartong, D. T., Berson, E. L. & Dryja, T. P. Retinitis pigmentosa. *The Lancet* 368, 1795-1809 (2006).
9. Salvi, S., Akhtar, S. & Currie, Z. Ageing changes in the eye. *Postgraduate medical journal* 82, 581-587 (2006).
10. McCulloch, D. L., et al. ISCEV Standard for full-field clinical electroretinography (2015 update). *Documenta ophthalmologica* 130, 1-12 (2015).
11. Seiple, W. H., Siegel, I. M., Carr, R. E. & Mayron, C. Evaluating macular function using the focal ERG. *Investigative ophthalmology & visual science* 27, 1123-1130 (1986).
12. Hood, D. C., Seiple, W., Holopigian, K. & Greenstein, V. A comparison of the components of the multifocal and full-field ERGs. *Visual neuroscience* 14, 533-544 (1997).
13. Hood, D. C., et al. Assessment of local retinal function in patients with retinitis pigmentosa using the multi-focal ERG technique. *Vision research* 38, 163-179 (1998).
14. Boye, S. E., Boye, S. L., Lewin, A. S. & Hauswirth, W. W. A comprehensive review of retinal gene therapy. *Molecular therapy* 21, 509-519 (2013).

15. Batabyal, S., et al. Sensitization of ON-bipolar cells with ambient light activatable multi-characteristic opsin rescues vision in mice. *Gene Therapy*, 1-15 (2020).
16. Mahato, B., et al. Pharmacologic fibroblast reprogramming into photoreceptors restores vision. *Nature* 581, 83-88 (2020).

What is claimed is:

1. A device comprising:
   i) an image-guided light stimulation beam allowing a variable spot size at a sample, for electrophysiological measurement of the sample,
   ii) an image-guided light stimulation beam assembly comprising:
   an imaging sub-assembly that provides illumination and collection of back-reflected light from the sample for imaging, and comprises near infrared (NIR) light from a low coherence source, and wherein the near infrared (NIR) light is able to be split into a sample beam and a reference beam for interferometric detection to obtain depth resolved images, and
   a light stimulation sub-assembly comprising of light beams of different wavelengths with controllable intensities and/or pulsation rates,
   iii) wherein a stimulation beam power at a sample plane ranges from 0.01 to 50 cd. $s/m^2$ for each individual stimulation light beam wavelength,
   iv) wherein the light stimulation beam is combinable with the sample beam and able to be directed to the sample,
   v) wherein the sample is selected from neurons or light-sensitive cells in-vitro or in-vivo,
   vi) wherein the region of interest for the electrophysiological measurement on the sample in response to variable spot stimulation is pre-selected and controlled by scanning mirrors for deflecting the light stimulation beam(s),
   vii) wherein the variable spot size is generated by a dynamic focusing element,
   viii) wherein the light stimulation is able to be targeted to the pre-selected region of interest on the sample,
   ix) wherein the light stimulation beam is able to be switched off during preselection of the region of interest for light stimulation, and wherein the preselection of the region of interest is based on morphologic/tomographic imaging,
   x) wherein the sample beam for morphologic/tomographic imaging is deliverable via fiber-optic or free-space, and is able to be collimated, and deflected to the sample by the scanning mirrors and optical components,
   xi) wherein the optical components are coated with an anti-reflection material for avoiding scattering and multiple reflections,
   xii) wherein the back-reflected sample beam for morphologic/tomographic imaging from the sample is able to be routed back to a detector,
   xiii) wherein a tomographic image is reconstructable by recording and analysis of interference between the back-reflected sample beam and the reference beam,
   xiv) wherein the morphologic/tomographic image is able to be marked with selected regions of variable sizes to match with the light stimulation spots for electrophysiological measurements,
   xv) wherein electrophysiological measurement is able to be conducted by electrodes connected to biosensing hardware,
   xvi) wherein the image guided light stimulation beam, allowing the variable spot size at the sample, for electrophysiological measurement can be a benchtop system or wearable system,
   xvii) wherein the wearable system for electrophysiological measurements comprises goggles or eye glasses, and
   xviii) wherein the device is for generating spatial-temporal multiplexed variable-spot light stimulated electrophysiological measurements to enable improved signal to noise ratio from averaging and reducing measurement time, wherein:
   i) the device is configured to stimulate a fraction of multiple non-overlapping spots among fractions of total number of spots of interest using a short burst of stimulation,
   ii) the device is configured to reduce a time gap between stimulations by stimulating another fraction of multiple spots,
   iii) the device is configured to change an order of synchronized stimulation among the fractions of the total number of spots of interest in each burst stimulation window,
   iv) the device is configured to measure electrophysiological signals arising from a single set of bursts of stimulation containing linear combination of signal responses from the total number of spots of interest, and
   v) the device is configured to solve linear equations based on location and time of stimulations and retrieve averaged signal from individual spots.

2. The device according to claim 1, comprising electrodes, wherein the image guided variable spot stimulation-electrophysiology assembly is configured to measure electroretinography (ERG) when the electrodes are placed in the cornea of a subject, and visually evoked potential (VEP) when the electrodes are placed in the brain or over the visual cortex of a subject.

3. The device according to claim 1, wherein the imaging light source is low coherence broadband light source or swept source for Optical coherence tomography (OCT) that is used in conjunction with a spectrometer-detector or point detector for tomographic imaging.

4. The device according to claim 1, wherein spatiotemporal guidance of light stimulation of the sample consists of OCT and/or fundoscope.

5. The device according to claim 1, wherein the image-guided light stimulation spot is configured to be expanded or contracted by scanning control of the deflecting mirrors and the dynamic focusing element, and by positioning in the selected area(s) of retina of a subject.

6. The device according to claim 1, wherein the multiple stimulation wavelengths of the image guided variable spot electrophysiology system allows probing of different photoreceptors' functions.

7. The device according to claim 1, wherein the multiple light stimulation beams are combinable to produce a mixed color stimulation.

8. The device according to claim 1, wherein the image guided variable spot electrophysiological measurement device enables functional mapping of the visual field using pattern stimulation.

9. The device according to claim 1, comprising multiple electrode channels for measuring electroretinogram and visually evoked potential simultaneously from a single stimulation(s).

10. The device according to claim 1, wherein the device is for generating stimulation frequency multiplexed measurement, and is configured to stimulate and record multiple light responding cell types with a different absorption spectrum at the same stimulation location simultaneously, wherein:
- i) the device is configured to combine multiple wavelength stimulation beams, modulated at different frequencies,
- ii) the device is configured to stimulate different light sensitive cells having distinct but separated absorption peaks,
- iii) the device is configured to extract a light response of different types of light activatable cells within the common stimulated area with a single measurement,
- iv) the device is configured to deconvolve a mixed response from individual cells by averaging an acquired electrophysiological signal of corresponding color stimulation time stamps, and/or
- v) the device is configured to reduce contributions of a frequency/wavelength dependent response of the other cell type by notch frequency filtering.

11. The device according to claim 1, wherein the device is configured to identify localized disease progression or therapeutic effect, and configured to measure using an image-guided variable spot electrophysiology system with multiple stimulation wavelengths, wherein:
- i) the device is configured to compare measurements at a baseline of healthy/normal and abnormal area(s) with identical stimulation parameters,
- ii) the device is configured to compare a spatially localized electrophysiology measurement to an earlier time point measurement at the same location(s) of the healthy/normal and abnormal area(s),
- iii) the device is configured to identify changes of various light sensitive cell type functions with matching stimulation wavelength and/or stimulation intensities,
- iv) the device is configured to map out an electrophysiological function of the visual field by different stimulation patterns comprising peripheral stimulation pattern and array stimulation pattern, and
- v) the device is configured to determine the progression of localized dystrophy or therapeutic improvements by a series of enlarging concentric circular stimulations and is able to assess a gradient of electrophysiological changes at localized disease region(s).

* * * * *